US008444994B2

(12) United States Patent
Hotez et al.

(10) Patent No.: US 8,444,994 B2
(45) Date of Patent: May 21, 2013

(54) MULTIVALENT ANTIHELMINTHIC VACCINE

(75) Inventors: Peter Hotez, Bethesda, MD (US); Alexander Loukas, Cairns (AU); Mark Pearson, Buderim (AU); Jeffrey Bethony, Minas Gerais (BR); Bin Zhan, North Potomac, MD (US); Gaddam Goud, Boyds, MD (US); Maria Elena Bottazzi, Washington, DC (US); David Diemert, Washington, DC (US); Ami Shah Brown, Halethorpe, MD (US); Peter Giacomautonio, Mansfield (AU)

(73) Assignees: The Albert B. Sabin Vaccine Institute, Washington, DC (US); The George Washington University, Washington, DC (US); The Council of the Queensland Institute of Medical Research, Queensland (AU)

( * ) Notice: Subject to any disclaimer, the term of this patent is extended or adjusted under 35 U.S.C. 154(b) by 61 days.

(21) Appl. No.: 12/999,132

(22) PCT Filed: Jun. 30, 2009

(86) PCT No.: PCT/US2009/049220
§ 371 (c)(1),
(2), (4) Date: Feb. 18, 2011

(87) PCT Pub. No.: WO2010/002867
PCT Pub. Date: Jan. 7, 2010

(65) Prior Publication Data
US 2011/0200640 A1 Aug. 18, 2011

Related U.S. Application Data

(60) Provisional application No. 61/077,256, filed on Jul. 1, 2008.

(51) Int. Cl.
*A61K 39/00* (2006.01)
*A61K 39/002* (2006.01)
*A61K 45/00* (2006.01)
*A61K 47/00* (2006.01)

(52) U.S. Cl.
USPC ............... 424/185.1; 424/192.1; 424/191.1; 424/265.1; 424/278.1; 424/184.1

(58) Field of Classification Search
None
See application file for complete search history.

(56) References Cited

U.S. PATENT DOCUMENTS

| 7,303,752 B2 * | 12/2007 | Hotez et al. ............... 424/191.1 |
| 2004/0001849 A1 | 1/2004 | Punnonen et al. |
| 2005/0042232 A1 | 2/2005 | Hotez et al. |

FOREIGN PATENT DOCUMENTS

| WO | WO 2007/014415 | 2/2007 |
| WO | WO 2007/014415 A1 * | 2/2007 |

OTHER PUBLICATIONS

Dalton et al., International Journal of Parasitology, 2003; 33: 621-640.*
Geiger, Acta Tropica, 2008; 108: 118-123.*
Hotez, Peter J et al., Multivalent Anthelminthic Vaccine to Prevent Hookworm and Schistosomiasis, Expert Rev. Vaccines, Aug. 2008, 745-752, 7-6, Expert Reviews Ltd, UK.
McManus, Donald P et al., Current Status of Vaccines for Schistosomiasis, Clinical Microbiology Reviews, Jan. 2008, 225-242, 21-1, American Society for Microbiology, USA.
Diemert, David J, Hookworm Vaccines, Vaccines, Dec. 4, 2007, 282-288, 2008:46(Jan. 15), Infectious Diseases Society of America, USA.
Pearson, Mark S, et al., Enhanced Protective Efficacy of a Chimeric Form of the Schistosomiasis Vaccine Antigen SM-TSP-2, PLOS Neglected Tropical Diseases, 1-10, 6-3-e1564, doi:10.1371/journal.pntd.0001564.
Knox, DP, Parasite Vaccines: Recent Progress in and Problems Associated with their Development, The Open Infectious Diseases Journal, 2010, 63-73, 4, Bentham Open, UK.

* cited by examiner

*Primary Examiner* — Vanessa L. Ford
*Assistant Examiner* — Lakia Tongue
(74) *Attorney, Agent, or Firm* — Whitham Curtis Christofferson & Cook, PC

(57) ABSTRACT

A multivalent anthelmintic vaccine targets both hookworm and schistosomiasis. The vaccine includes, at a minimum, a recombinant third-stage larval hookworm antigen, a recombinant adult stage hookworm antigen, and a recombinant schistosome antigen. Preferably, the hookworm antigens are *Necator americanus* antigens, although antigens from other hookworm species (e.g. *Ancylostoma duodenale*) may also be employed. The schistosome antigen is preferably a *Schistosoma mansoni* or a *Schistosoma haematobium* antigen although antigens from other schistosome species (e.g. *Schistosoma japonicum*) may also be employed. In some cases full or partial sequences of schistosome antigens may be fused with full or partial sequences of hookworm {*Necator americanus*) to produce recombinant chimeric antigens.

4 Claims, 23 Drawing Sheets gaaaatcaca atgatgtctt ctatcacatg tttggttctt ctctcgattg cagcgtactc caaagccggt tgtcctgaca
atggaatgtc agaggaagca cggcaaaaat tccttgaatt gcacaattcg ttgagaagtt cggttgcatt gggacaggcc
aaggatggag ctggtggaaa tgccccgaaa gctgctaaga tgaagacgat ggcatacgat tgcgaagttg
aaaagactgc aatgaataac gcgaaacaat gtgtattcaa gcactcgcaa cctaaccaaa ggaaaggatt
gggagagaat atatttatgt cttcggatag cggtatggac aaagcaaagg ctgctgagca ggctagcaaa gcttggttcg
gcgaacttgc agaaaaagga gttggacaga atcttaagct tacaggaggc ttgttcagca gaggagtcgg gcactataca
cagatggtat ggcaagaaac cgttaagctt ggatgctatg tggaagcgtg ctcaaatatg tgttatgtgg tgtgccagta
cggtcctgct ggaaatatga tgggcaagga tatctacgag aaaggagaac cgtgttcgaa atgtgagaat
tgcgacaagg agaagggact ctgcagtgct tgattagttg tgttcagtga agctcattac gctcacatac tttaacaaat
cgtagtgatc tgtagttgct ttaatattca aataaacatg atgccagcaa aaaaaaaaaa aaa (SEQ IN NO: 1)

*Figure 1A*

Met Ser Ser Ile Thr Cys Leu Val Leu Leu Ser Ile Ala Ala Tyr Ser Lys Ala Gly Cys Pro
Asp Asn Gly Met Ser Glu Glu Ala Arg Gln Lys Phe Leu Glu Leu His Asn Ser Leu Arg
Ser Ser Val Ala Leu Gly Gln Ala Lys Asp Gly Ala Gly Gly Asn Ala Pro Lys Ala Ala Lys
Met Lys Thr Met Ala Tyr Asp Cys Glu Val Glu Lys Thr Ala Met Asn Asn Ala Lys Gln
Cys Val Phe Lys His Ser Gln Pro Asn Gln Arg Lys Gly Leu Gly Glu Asn Ile Phe Met Ser
Ser Asp Ser Gly Lys Ala Lys Ala Ala Glu Gln Ala Ser Lys Ala Trp Phe Gly Glu Leu Ala
Glu Lys Gly Val Gly Gln Asn Leu Lys Leu Thr Gly Gly Leu Phe Ser Arg Gly Val Gly
His Tyr Thr Gln Met Val Trp Gln Glu Thr Val Lys Leu Gly Cys Tyr Val Glu Ala Cys Ser
Asn Met Cys Tyr Val Val Cys Gln Tyr Gly Pro Ala Gly Asn Met Met Gly Lys Asp Ile
Tyr Glu Lys Gly Glu Pro Cys Ser Lys Cys Glu Asn Cys Asp Lys Glu Lys Gly Leu Cys
Ser Ala (SEQ IN NO: 2)

*Figure 1B*

```
AAAAGCCTCCATAGTCATGCTCAAGCTCGTTGCACTCGTTTGCCTGGTTGCAATCTGCT
TCGCTCAGGGACCACAAGGACCCCCTCCGTTCCTGCAAAGTGCTCCAGCGGCTGTTCAA
CAAGACTTCGACAAGCTCTTCGTCAATGCTGGCTCCAAGACTGATGCAGAAATCGACAA
AATGGTCCAAGATTGGGTTGGCAAACAAGATGCATCCATCAAGACCGCATTCGATGCGT
TCGTGAAGGAAGTGAAAGCCGCTCAAGCGCAAGGTGAAGCTGCCCATCAGGCTGCTATC
GCCAAGTTCAGCGCAGAGGCCAAAGCGGCTGATGCCAAGCTGAGCGCAATTGCGAACGA
CAGGTCGAAGACAAACGCGCAAAAGGGAGCTGAGATCGACTCGGTACTCAAGGGACTTC
CTCCAAATGTCCGCACAGAGATCGAAAACGCCATGAAAGGATAAGAAGTCTCTATTTTG
TATATATGAACCGATAAATATGCACAATAAAAAAAAAAAAAAAAAAAAAAAAAAA
(SEQ IN NO: 3)
```

*Figure 2A*

```
MLKLVALVCLVAICFAQGPQGPPPFLQSAPAAVQQDFDKLFVNAGSKTDAEIDKMVQDW
VGKQDASIKTAFDAFVKEVKAAQAQGEAAHQAAIAKFSAEAKAADAKLSAIANDRSKTN
AQKGAEIDSVLKGLPPNVRTEIENAMKG*
(SEQ IN NO: 4)
```

*Figure 2B*

```
AGCGTTCATCGACGACTCTTTCATCAAGCTCGTCGTCATGTGACATCGGTATCGCTTTC
GCGTCAGCCAACACTTCGTGAACGACTGATCGCAAGTGGCAGTTGGGAGGATTACCAGA
AACAACGCTACCATTATCAAAAGAAAATTCTAGCAAAATATGCTGCTAACAAAGCGTCA
AAGTTACAATCTGCAAACGAGATCGATGAATTGCTCCGGAACTATATGGATGCACAATA
CTATGGTGTCATCCAAATTGGACTCCAGCTCAGAATTTCACTGTGATCTTCGACACGG
GTTCCTCAAATCTATGCGTACCGTCAAGAAAGTGTCCATTCTATGACATTGCATGTATG
CTTCATCATCGTTATGACTCCGGAGCCTCGTCAACCTGCAAGGAAGATGGGCGCAAGAT
GGCTATTCAGTATGGAACTGGATCTATGAAAGGATTCATTTCTAAGGATATTGTTTGTA
TTGCTGGAATTTGCGCTGAAGAACAACCTTTCGCGGAGGCTACAAGTGAACCTGGTCTT
ACATTTATCGCTGCTAAGTTTGATGGAATCCTTGGAATGGCATTCCCGGAAATTGCTGT
TCTCGGTGTAACTCCTGTCTTCCATACGTTCATTGAACAGAAGAAAGTTCCTAGCCCTG
TGTTTGCTTTCTGGCCGAATAGGAATCCAGAGTCGGAAATTGGAGGAGAGATTACCTTT
GGTGGTGTGGATACCCGACGTTATGTTGAACCAATTACATGGACACCAGTGACACGTCG
TGGATATTGGCAATTCAAAATGGATATGGTACAAGGTGGTTCATCGTCCATTGCGTGTC
CGAATGGATGCCAAGCTATCGCTGATACTGGCACTTCTCTTATTGCTGGACCGAAGGCA
CAGGTTGAGGCAATCCAGAAATATATCGGAGCAGAGCCGCTTATGAAAGGAGAATACAT
GATTCCTTGCGACAAAGTACCATCCCTTCCTGATGTTTCGTTCATCATCGATGGCAAGA
CGTTTACACTCAAAGGGGAAGATTACGTTCTAACCGTGAAAGCCGCTGGTAAATCAATC
TGTTTGTCTGGCTTCATGGGAATGGACTTCCCAGAGAAGATCGGCGAATTGTGGATCCT
TGGAGATGTTTTCATTGGAAAATACTACACCGTCTTCGATGTTGGTCAGGCACGTGTTG
GATTTGCTCAAGCAAAGTCAGAAGATGGATTCCCTGTTGGGACCCCCGTTCGAACATTC
AGACAGCTTCAGGAAGACAGCGATAGCGACGAGGACGATGTATTTACTTTTTAA
(SEQ IN NO: 5)
```

*Figure 3A*

```
SVHRRLFHQARRHVTSVSLSRQPTLRERLIASGSWEDYQKQRYHYQKKILAKYAANKAS
KLQSANEIDELLRNYMDAQYYGVIQIGTPAQNFTVIFDTGSSNLWVPSRKCPFYDIACM
LHHRYDSGASSTCKEDGRKMAIQYGTGSMKGFISKDIVCIAGICAEEQPFAEATSEPGL
TFIAAKFDGILGMAFPEIAVLGVTPVFHTFIEQKKVPSPVFAFWPNRNPESEIGGEITF
GGVDTRRYVEPITWTPVTRRGYWQFKMDMVQGGSSSIACPNGCQAIADTGTSLIAGPKA
QVEAIQKYIGAEPLMKGEYMIPCDKVPSLPDVSFIIDGKTFTLKGEDYVLTVKAAGKSI
CLSGFMGMDFPEKIGELWILGDVFIGKYYTVFDVGQARVGFAQAKSEDGFPVGTPVRTF
RQLQEDSDSDEDDVFTF
(SEQ IN NO: 6)
```

*Figure 3B*

```
GGCACGAGGGGAGATGGCTCGACTTGTATTCCTACTCGTACTATGTACTCTGGCTGCAC
AAGCGTTCATCGACGACTCTTTCATCAAGCTCGTCGTCATGTGACATCGGTATCGCTTT
CGCGTCAGCCAACACTTCGTGAACGACTGATCGCAAGTGGCAGTTGGGAGGATTACCAG
AAACAACGCTACCATTATCGAAAGAAAATTCTAGCAAAATATGCTGCTAACAAAGCGTC
AAAGTTACAATCTGCAAACGAGATCGATGAATTGCTCCGGAACTATATGGATGCACAAT
ACTATGGTGTCATCCAAATTGGGACTCCAGCTCAGAATTTCACTGTGATCTTCGACACG
GGTTCCTCAAATCTATGGGTACCGTCAAGAAAGTGTCCATTCTATGACATTGCATGTAT
GCTTCATCATCGTTATGACTCCGGAGCCTCGTCAACCTACAAGGAAGATGGGCGCAAGA
TGGCTATTCAGTATGGAACTGGATCTATGAAAGGATTCATTTCTAAGGATATTGTTTGT
ATTGCTGGAATTTGCGCTGAAGAACAACCTTTCGCGGAGGCTACAAGTGAACCTGGTCT
TACATTTATCGCTGCTAAGTTTGATGGAATCCTTGGAATGGCATTCCCGGAAATTGCTG
TTCTCGGTGTAACTCCTGTCTTCCATACGTTCATTGAACAGAAGAAAGTTCCTAGCCCT
GTGTTTGCTTTCTGGCTGAATAGGAATCCAGAGTCGGAATTGGAGGAGAGATTACCTT
TGGTGGTGTGGATACCCGACGTTATGTTGAACCAATTACATGGACACCAGTGACACGTC
GTGGATATTGGCAATTCAAAATGGATATGGTACAAGGTGGTTCATCGTCCATTGCGTGT
CCGAATGGATGCCAAGCTATCGCTGATACTGGCACTTCTCTTATTGCTGGACCGAAGGC
ACAGGTTGAGGCAATCCAGAAATATATCGGAGCAGAGCCGCTTATGAAAGGAGAATACA
TGATTCCTTGCGACAAAGTACCATCCCTTCCTGATGTTTCGTTCATCATCGATGGCAAG
ACGTTTACACTCAAAGGGGAAGATTACGTTCTAACCGTGAAAGCCGCTGGTAAATCAAT
CTGTTTGTCTGGCTTCATGGGAATGGACTTCCCAGAGAAGATCGGCGAATTGTGGATCC
TTGGAGATGTTTTCATTGGAAAATACTACACCGTCTTCGATGTTGGTCAGGCACGTGTT
GGATTTGCTCAAGCAAAGTCAGAAGATGGATTCCCTGTTGGCACCCCCGTTCGAACATT
CAGACAGCTTCAGGAAGACAGCGATAGCGACGAGGACGATGTATTTACTTTTTAAGTAG
TGTTAACATCTCCAACGTGCTCTGTTACTTCTACGTGTACCATGTTTCACGTGTTTGCT
CATTTGATAAATTATTATCTTCCCT
(SEQ IN NO: 7)
```

*Figure 3C*

```
MARLVFLLVLCTLAAASVHRRLFHQARRHVTSVSLSRQPTLRERLIASGSWEDYQKQRY
HYRKKILAKYAANKASKLQSANEIDELLRNYMDAQYYGVIQIGTPAQNFTVIFDTGSSN
LWVPSRKCPFYDIACMLHHRYDSGASSTYKEDGRKMAIQYGTGSMKGFISKDIVCIAGI
CAEEQPFAEATSEPGLTFIAAKFDGILGMAFPEIAVLGVTPVFHTFIEQKKVPSPVFAF
WLNRNPESEIGGEITFGGVDTRRYVEPITWTPVTRRGYWQFKMDMVQGGSSSIACPNGC
QAIADTGTSLIAGPKAQVEAIQKYIGAEPLMKGEYMIPCDKVPSLPDVSFIIDGKTFTL
KGEDYVLTVKAAGKSICLSGFMGMDFPEKIGELWILGDVFIGKYYTVFDVGQARVGFAQ
AKSEDGFPVGTPVRTFRQLQEDSDSDEDDVFTF*
(SEQ IN NO: 8)
```

*Figure 3D*

```
GTTAAAGCCGTGTAAGCAACAGGGTTCTTTGTGATGTTAACTCTCGCTGCACTTCTGAT
TTCTGTTTCGCTGGTTGAGCCGACAGGCATAGGTGAGTTTCTTGCTCAACCAGCACCTG
CATATGCTAGAAGACTCACAGGGCAGGCCCTTGTTGACTACGTCAATTCGCACCACTCA
TTGTACAAGGCCAAATATTCACCAGATGCTCAAGAACGCATGAAATCTAGAATTATGGA
TTTGAGTTTCATGGTTGATGCGGAAGTCATGATGGAAGAAATGGACCAGCAGGAGGATA
TAGATCTCGCTGTTTCTTTACCTGAAAGTTTCGACGCTCGTGAAAAATGGCCAGAATGT
CCTTCAATAGGATTAATCCGTGATCAGTCCGCCGGTGGAGGATGTTGGGCAGTATCCTC
AGCAGAGGTGATGACCGACAGGATCTGTATACAATCAAATGGAACAAAGCAGGTGTATG
TTTCCGAAACGGATATCTTATCATGCTGTGGACAACGTTGCGGTAGCGGGTGTACCTCA
GGTGTGCCACGTCAAGCTTTCAACTATGCAATTCGTAAAGGTGTTTGCAGTGGAGGACC
ATATGGAACGAAGGGTGTTTGCAAACCCTATCCTTTCTATCCATGCGGCTATCATGCTC
ATCTGCCATATTATGGACCATGTCCAGATGGTATGTGGCCTACGCCAACATGCGAAAAG
GCATGTCAATCCGACTATACTGTTCCGTACAACGATGACAGGATCTTCGGCAGCAAAAC
TATTGTCTTGACGGGAGAGGAAAAAATTAAGCGAGAGATTTTCAATAACGGACCATTGG
TAGCCACGTATACAGTTTACGAAGATTTCGCTTATTACAAGAATGGAATTTACATGACT
GGTCTCGGTAGAGCGACAGGCGCACATGCAGTCAAAATTATTGGCTGGGGTGAAGAAAA
TGGAGTCAAGTATTGGTTGATTGCAAACTCGTGGAACACTGATTGGGGAGAGAATGGCT
TCTTCCGCATGCTTCGTGGAACAAACCTTTGCGATATTGAACTAAGCGCGACTGGAGGA
ACGTTCAAGGTGTGAACGTGATCGAAAAGAACGATTTTGAACAAAATCTTCCCGTATT
GTCATCAAAAAAA
(SEQ IN NO: 9)
```

*Figure 4A*

```
MLTLAALLISVSLVEPTGIGEFLAQPAPAYARRLTGQALVDYVNSHHSLYKAKYSPDAQ
ERMKSRIMDLSFMVDAEVMMEEMDQQEDIDLAVSLPESFDAREKWPECPSIGLIRDQSA
GGGCWAVSSAEVMTDRICIQSNGTKQVYVSETDILSCCGQRCGSGCTSGVPRQAFNYAI
RKGVCSGGPYGTKGVCKPYPFYPCGYHAHLPYYGPCPDGMWPTPTCEKACQSDYTVPYN
DDRIFGSKTIVLTGEEKIKREIFNNGPLVATYTVYEDFAYYKNGIYMTGLGRATGAHAV
KIIGWGEENGVKYWLIANSWNTDWGENGFFRMLRGTNLCDIELSATGGTFKV*
(SEQ IN NO: 10)
```

*Figure 4B*

```
ttaattctta ttgctctggt ggtgacggcg ttggctcaac agccgctttc
actaaggag tatctggaac agccgatacc agaggaggca gagaatcttt
cggagaagc gtttgcggag tttctgaaca aacgacaatc gttttcacg
gctaagtaca cgccaaatgc tttaaacatt cttaaaatgc gtgtgatgga
atcgagattc ctggacaatg aagaaggtga aatgctaaaa gaggaggaca
tggatttcag tgaagaaatt cctgttagtt ttgatgctcg agacaaatgg
cccaaatgca cctccatagg atttatccgt gatcaatcac actgtggttc
atgctgggca gtatcgtcag cagaaacgat gtcagatcga ctctgcgtgc
aatcaaacgg tacaattaag gtacttctat ccgatacgga catccttgcc
tgttgcccga attgtggtgc tggatgtgga ggaggccaca caattcgagc
gtgggaatat tttaagaaca caggcgtttg cactggcgga ctatatggaa
caaaggattc ctgcaaacca tacgctttct atccatgtaa agacgaaagt
tacggaaagt gccccaagga ttcttttcca acaccaaaat gtcgaaaaat
ttgtcagtat aaatacagta agaagtacgc cgacgacaaa tactacgcga
attccgcata tcgaattcca cagaatgaga cgtggatcaa attggagatc
atgagaaacg ggcctgtgac agcatcattc aggatttatc cggattttgg
gttttacgaa aaggagtttt atgtgacttc aggcggaagg gaactaggtg
ggcacgcgat taaaatcatt ggatggggaa cggaaaaagt aaacggaact
gacctaccctt actggttgat tgctaactct tggggtactg actggggaga
gaataacggc tatttccgca tacttcgcgg acaaaatcac tgccaaatag
aacagaaagt tatcgccggt atgataaaag taccacaacc gaaatccgcc
ggtccaccac ttcaacccaa tccttcaagc tgaaccaagt tgtagtattg
tccccatcaa tccaagcatt tcttggggtg atactttac gaataaaaac
tacattataa aaaaaaaaaa aaaaaaa
(SEQ ID NO: 11)
```

*Figure 5A*

```
LILIALVVTA LAQQPLSLKE YLEQPIPEEA ENLSGEAFAE FLNKRQSFFT AKYTPNALNI
LKMRVMESRF LDNEEGEMLK EEDMDFSEEI PVSFDARDKW PKCTSIGFIR DQSHCGSCWA
VSSAETMSDR LCVQSNGTIK VLLSDTDILA CCPNCGAGCG GGHTIRAWEY FKNTGVCTGG
LYGTKDSCKP YAFYPCKDES YGKCPKDSFP TPKCRKICQY KYSKKYADDK YYANSAYRIP
QNETWIKLEI MRNGPVTASF RIYPDFGFYE KGVYVTSGGR ELGGHAIKII GWGTEKVNGT
DLPYWLIANS WGTDWGENNG YFRILRGQNH CQIEQKVIAG MIKVPQPKSA GPPLQPNPSS
(SEQ ID NO: 12)
```

*Figure 5B*

```
tcgttgaggc gttatttcaa gcttctctcg cctcgatttc agattctcca
attgtttcag tgaatcgtgg aacagtcaat ctcacttttg tgagatccaa
tgaaagctaa ttttgcgttg gtcgtcgtcc ttctggcaat aaaccagtta
tatgcagatg agctgcttca caaacaagag tccgaacacg gacttagtgg
ccaagcgctc gttgactacg ttaattcgca ccaatcactt ttcaaaacag
aatattcgcc aaccaatgaa caattcgtta aagcccgtat aatggacata
aagtatatga ctgaggctag ccacaaatat ccaagaaagg cattaatct
gaacgttgaa ctccctgaaa ggtttgacgc acgtgaaaaa tggccacatt
gcgcctccat cggtctcatt cgcgatcact ctgcttgcgg atcgtgttgg
gctgtatcgg cagcgtcggt tatgtcagat cgactctgta tccagacgaa
cggcacaaac cagaagatcc tttcgtcggc ggacatcctt gcgtgttgtg
gagaagactg tggctcagga tgcgaaggcg ttatccgat tcaggcgtac
ttctacctgg aaaatactgg agtatgtagt ggaggagagt atcgagaaaa
gaatgtatgc aaaccatatc ccttttatcc gtgtgacgga actatggac
catgccccaa ggagggtgcg ttcgacactc caaagtgtcg gaaaatatgt
cagttccgat atcctgttcc atacgaagaa gataaagtgt ttggaaaaaa
ttcacacatc cttctgcaag acaacgaggc aagaatcaga caggaaattt
tcataaacgg accagtggga gctaattttt acgttttcga agactttata
cactacaagg aagggattta taagcagaca tatgggaaat ggataggagt
acatgcaatc aaacttattg gttggggcac agaaaatgga acagattatt
ggttggttgc taactcgtac aactacgact ggggagagaa tggcaccttc
cgcattcttc gtggaactaa tcactgtttg atagaatcac aagtgatcgc
aacggagatg attgtatgaa tgtctaatga acgattggtc gcatgccgat
ctctgaagta aatgtgtta atcaaaaaaa a
(SEQ IN NO: 13)
```

Figure 6A

```
MKANFALVVVLLAINQLYADELLHKQESEHGLSGQALVDYVNSHQSLFKTEYSPTNEQF
VKARIMDIKYMTEASHKYPRKGINLNVELPERFDAREKWPHCASIGLIRDHSACGSCWA
VSAASVMSDRLCIQTNGTNQKILSSADILACCGEDCGSGCEGGYPIQAYFYLENTGVCS
GGEYREKNVCKPYPFYPCDGNYGPCPKEGAFDTPKCRKICQFRYPVPYEEDKVFGKNSH
ILLQDNEARIRQEIFINGPVGANFYVFEDFIHYKEGIYKQTYGKWIGVHAIKLIGWGTE
NGTDYWLVANSYNYDWGENGTFRILRGTNHCLIESQVIATEMIV
(SEQ IN NO: 14)
```

Figure 6B

```
tagataataa tcttttttgca cgtcagagaa tttctttgat aaaaccacaa
ttaaacaatc tcagcgctgt aaacacgtgc aaaactactc gttcatttct
cttcactttc cctccaaaac caaacattca agagaagcat gataaccatc
attaccctat tgcttatcgc ttctacagtg aagtcactaa cagtggagga
gtacttggcc cgaccagtgc cggaatatgc cacaaaactg acaggacaag
cctacgttga ctatgttaat cagcatcaat cattctacaa ggctgaatat
tccccgctgg ttgaacagta tgccaaagct gtgatgagat ctgagtttat
gacgaagccg aaccaaaatt atgtggtgaa ggacgtagat ctaaacatca
atcttccaga aaccttcgac gcaagggaaa aatggccaaa ctgcacatca
ataaggacaa ttcgcgatca gtccaattgt ggatcatgtt gggcagtatc
agcggcgtcg gtaatgtcag atcgtttatg catacagtcg aacggcacaa
tacagtcatg ggcttctgat acggatattc tatcatgttg ctggaattgc
ggaatgggat gcgatggagg tagaccgttt gcggcgttct ttttcgcgat
agacaatggt gtatgcactg gaggaccttt cagagagcca aacgtgtgca
aaccatacgc tttctatcca tgcggtcgcc accaaaacca gaaatacttc
ggaccttgtc caaaagagct ctggcccact ccaaaatgtc ggaaaatgtg
tcaactaaaa tataatgtgg cctacaaaga cgataaaatt tacgggaatg
atgcatacag tctccctaac aatgagacac gaatcatgca agaaattttc
acaaatggac ctgtagtggg atcattcagc gtgtttgctg actttgcaat
ttataagaaa ggagtatatg tgagtaatgg aattcagcag aatggggctc
atgcagtcaa aattattggt tggggtgtgc aggatggact aaaatattgg
ttgattgcta attcctggaa caatgactgg ggagacgaag gctatgtccg
gttccttcgt ggagataacc actgtggaat tgaatcaagg gtggtgacag
gaactatgaa agtgtaaaac aataattagt ctttcctga cgatttcaaa
taaaatcttt gccactaaaa aaaaaaaaaa aaaaaa
(SEQ IN NO: 15)
```

*Figure 7A*

```
MITIITLLLIASTVKSLTVEEYLARPVPEYATKLTGQAYVDYVN
QHQSFYKAEYSPLVEQYAKAVMRSEFMTKPNQNYVVKDVDLNINLPETFDAREKWPNC
TSIRTIRDQSNCGSCWAVSAASVMSDRLCIQSNGTIQSWASDTDILSCCWNCGMGCDG
GRPFAAFFFAIDNGVCTGGPFREPNVCKPYAFYPCGRHQNQKYFGPCPKELWPTPKCR
KMCQLKYNVAYKDDKIYGNDAYSLPNNETRIMQEIFTNGPVVGSFSVFADFAIYKKGV
YVSNGIQQNGAHAVKIIGWGVQDGLKYWLIANSWNNDWGDEGYVRFLRGDNHCGIESR
VVTGTMKV
(SEQ IN NO: 16)
```

*Figure 7B*

```
AAGTGATGGTTCATTACAAGTTAACCTACTTCGCTATACGTGGAGCCGGAGAATGTGCA
AGACAGATCTTCGCACTTGCCGATCAGGAATTCGAGGATGTCCGTTTAGACAAAGAGCA
GTTCGCAAAAGTGAAGCCTGATTTGCCTTTCGGACAGGTTCCAGTCCTTGAAGTCGATG
GCAAGCAACTGGCTCAATCCCTTGCGATTTGCCGCTATCTGGCCAGGCAGTTCGGTTTC
GCAGGCAAATCAACGTTCGATGAAGCCGTAGTCGACTCTTTAGCAGACCAGTATTCTGA
CTATCGCGTCGAGATCAAGTCGTTCTTCTACACTGTCATTGGAATGCGAGAAGGTGATG
TGGAGCAACTCAAAAAAGAAGTGTTACTTCCTGCTCGCGATAAATTCTTCGGATTCATC
ACTAAATTCCTTAAGAAAAGCCCTTCTGGTTTCCTTGTCGGTGACTCACTGACGTGGGT
GGACCTCTTGGTCTCGGAGCACAATGCTACAATGCTTACGTTTGTACCAGAGTTCCTTG
AAGGCTATCCTGAAGTAAAAGAGCACATGGAAAAGATACGAGCGATTCCGAAACTGAAG
AAATGGATCGAAACCCGACCAGAGACATTGTTCTAATTTGTAGTGATGTTATCCTACTT
GTTCTGATCTATTTGAGTTATCTTCATTGTCAACAGAAATTCATTATTGGCTTGCAGTA
ATAACCGTTATTCAGGCACTTGAAATCCACTAGTTATTTCTTTCCATAAGCTACATTCT
CAGATGTATGTATGAGGATAAA
(SEQ IN NO: 17)
```

*Figure 8A*

```
MVHYKLTYFAIRGAGECARQIFALADQEFEDVRLDKEQFAKVKPDLPFGQVPVLEVDGK
QLAQSLAICRYLARQFGFAGKSTFDEAVVDSLADQYSDYRVEIKSFFYTVIGMREGDVE
QLKKEVLLPARDKFFGFITKFLKKSPSGFLVGDSLTWVDLLVSEHNATMLTFVPEFLEG
YPEVKEHMEKIRAIPKLKKWIETRPETLF*
(SEQ IN NO: 18)
```

*Figure 8B*

```
aaatggctct tggttgtggg tataagtgtt tgcagtgttt gctaattatt ttcaactgtg gagcattcat atgtggtctc gggctgattg tggttggtgc acttgggctc cattctgttg taaatcactg gagcgaaatt gaacccccac tacaatctct tattatcttc attattgctc tcggatgctt cttatttgtt ttgggggctt tagggatgtt tggagcatgc atgaagaatg tttgtttatt aacgacgtat tgcattcttc tatcaatttt aatggttgcc gaaatagcag caggaatatt tgctatagta gaaaagccca aggtcaaaaa acacatcact agtgcattaa aaaaattagt agataagtac cgtaatgacg aacatgttcg aaaagttttt gatgaaatcc aacaaaaatt acattgctgt ggtgctgact ctcctaaaga ttatggcgaa aatccaccga catcatgttc aaaagatggc gtacaattta cagagggatg tattaaaaag gtcagcgatc taagcaaagc gcacctcaat gctatcatag ttagcgtgtt tctgttcgca ttggtccaaa tgatttgtct agtatttgca gtatgtgttc tattggctat aaagcgcggt gacgatgaat acaatgacat tacgaaaacg cttagtgaaa aaataaaccg aaaacaacca ttaaaaaatt aa
(SEQ IN NO: 19)
```

*Figure 9A*

```
MALGCGYKCL QCLLIIFNCG AFICGLGLIV VGALGLHSVV NHWSEIEPPL

QSLIIFIIAL GCFLFVLGAL GMFGACMKNV CLLTTYCILL SILMVAEIAA

GIFAIVEKPK VKKHITSALK KLVDKYRNDE HVRKVFDEIQ QKLHCCGADS

PKDYGENPPT SCSKDGVQFT EGCIKKVSDL SKAHLNAIIV SVFLFALVQM

ICLVFAVCVL LAIKRGDDEY NDITKTLSEK INRKQPLKN
(SEQ IN NO: 20)
```

*Figure 9B*

```
atgaaaagtg gctgggagta tattggaatc ttttgtaca ttatggtgaa tattctggat
aaacaacgat gtcattcagt gcgttgctac gtctgtgatt attgtccgat agtaacaagc
gtatcaatat cagaagagaa caactgtaca tcttgctcaa cggctggtta taattattcg
attcacagaa tatgcgtgtt taaggatggc atacccatta acttcccaaa cgaaaatcga
acgcagtgta acactgattt gtgtaacggg ttaacagttg ataacactgg aaaaattcca
tcagttccta tagcaaatcc atttcgttgc tatacgtgtt tgaattgtac aaaaagtaac
caaaaggtac ttagcggttg tggtgcatgt gtgacaactc gtggttctgg aattatcagt
aaattttgtg gaactacatg tgaagattg tatattgacg atcaaattag ttgttgctca
acagatctat gtaacggaat gacaaaatta tctattcatc gtcatgttat tattgttctg
tttgtttgca taggaatcag taaatacatt ctatga
(SEQ IN NO: 21)
```

Figure 10A

```
mksgweyigi flyimvnild kqrchsvrcy vdycpivts vsiseennct scstagynys
ihricvfkdg ipinfpnenr tqcntdlcng ltvdntgkip svpianpfrc ytclnctksn
qkvlsgcgac vttrgsgiis kfcgttcerl yiddqisccs tdlcngmtkl sihrhviivl
fvcigiskyi l
(SEQ IN NO: 22)
```

Figure 10B

```
ATGGCTCTTGGTTGTGGGTATAAGTGTTCGCAATGTTTGCTAGTTATTTTCAATTGTGGAGCGTT
CATATGTGGTCTCGGGCTGATTGTGGTTGGTGCACTTGGGCTCCATTCTGTTGTAAATCACTGGA
AAGACATTGAACCTCCATTACAATCGCTTATTATCTTTATTATTGTCCTCGGATGCTTCTTATTT
GTTTTGGGGGCCTTAGGAATGTTTGGCGCCTGCACGAAGAATGTGTGTTTATTAACAACGTATTG
TATTCTTTTATCAATTTTGATAGTTGCCGAAATAGCAGCAGGAATATTTGCAATATTGGAAAAGC
CAAAGGTAAAAAAACACGTCACTGATGCATTAAGAGAATTCGTAAAAGAGTACTCTCACGACGAA
CATGTTAGCAAAGTTCTTGATGAAGTTCAACAGAAATTACAATGCTGTGGTGCTGATTCTTCAAA
AGATTATGTCACTCCACCACCGGAATCCTGTTTCAAAGATGGCCAAATATTTAAAGAGGGATGCG
TTAAAAAGGTCAGTGATCTAAGCAAAATGCACCTCAATGCTATCATAATTAGCGTATTTCTGTTC
TCATTGGTCCAAATGATTTGTCTGGTATTTGCAGTATGTGTTCTATTGGCTGTAAAGCGCGGTGA
TGATGAATAG
(SEQ IN NO: 23)
```

*Figure 11A*

```
MALGCGYKCSQCLLVIFNCGAFICGLGLIVVGALGLHSVVNHWKDIEPPLQSLIIFIIVL
GCFLFVLGALGMFGACTKNVCLLTTYCILLSILIVAEIAAGIFAILEKPKVKKHVTDALR
EFVKEYSHDEHVSKVLDEVQQKLQCCGADSSKDYVTPPPESCFKDGQIFKEGCVKKVSDL
SKMHLNAIIISVFLFSLVQMICLVFAVCVLLAVKRGDDE
(SEQ IN NO: 24)
```

*Figure 11B* atgtttctatcacaattacaaaagtattggaataatatatttattatatccaatctacta
ttcattgtattcgatatagctttattggcattacctattagaacattagatgtcttagct
aattacaatacaattttagattattttaaaccagtgatctttccagttgtcatctttaca
gggattcttggactattgagtgtttttataggtttcattggattatggaaaaagaagact
gttttcatttggtgcacattgtcgggttgactattgcaacaattattgaaatctctata
tctataagatcaagtttacggaaaaatcagttcttcaaagtagctaatcaatcattatgg
aattctattcaatattatgaaaaacatccaaattatgaaaatcaagtggataatctacaa
agagagttttttgttgtggtgttagatcatatacagattataaaagaccggtaattacc
ctaccactttcttgtaaaacaggcaattcaattcatccaaaaggttgtgctgaagcccta
tatgattatatacaacattgtatcatgataataatatatatgcattgcattcgctatc
attaaagctatctatttggccacttctattcttctatatcgtaaatctgagaagaataat
ttatctgtataa
(SEQ IN NO: 25)

Figure 12A

MFLSQLQKYWNNIFIISNLLFIVFDIALLALPIRTLDVLANYNTILDYFKPVIFPVVIFT
GILGLLSVFIGFIGLWKKKTVFILVHIVGLTIATIIEISISIRSSLRKNQFFKVANQSLW
NSIQYYEKHPNYENQVDNLQREFFCCGVRSYTDYKRPVITLPLSCKTGNSIHPKGCAEAL
YDYIQHCIMIIIYICIAFAIIKAIYLATSILLYRKSEKNNLSV
(SEQ IN NO: 26)

Figure 12B

```
atgttgtgcaacctaccatgtcgaattgttttgattgttatgaacactgtcagcatgatt
gtagggctggtactgctcatacttggagccttgatggtttggggtcaaagtgttattcaa
tccttgttgaataatttcataaccaacctaattaatcagtacattaaaggaactgatagt
ggacaaattaatgaaatggtcacacgaatactgacgtctacttctccagttggtatggca
gtttttatactaggtgctgtttgtacaggtatctcgttgtttggttattgtggagcctgt
tgtaatatgaagatattactttatatatacgcaattttagtaggagcattggcacttgct
ttcctgatcacattcagtgtgtacttctctcgtaaagatgagattggaaacagagcaatt
gacctattcgagacaagtgtcaagaattatcaatcaatggcagcaaatacaattgacagc
ttagtggttggcttaatctcacctccacttcaatgttgtggtgtgaataatggagatgac
tttacaacttcacctaatttctggagaaatgacacttacggtggtaaaacatataataat
attgcatatcctgtagtatgttgcaaattgaatcaaaattatgcaattattgattctaca
tgtccagatcaatttaatgaaaataacagtaattataaaactggttgtagaggtccatta
aaagaacttttccttaaatatatggactttgtagcttatggattaattgcggcatttgtt
atattggtaagtattattgcttttataaaaatttatttcgagttactttttttcgtcttt
aattaa
(SEQ IN NO: 27)
```

Figure 13A

```
MLCNLPCRIVLIVMNTVSMIVGLVLLILGALMVWGQSVIQSLLNNFITNLINQYIKGTDS
GQINEMVTRILTSTSPVGMAVFILGAVCTGISLFGYCGACCNMKILLYIYAILVGALALA
FLITFSVYFSRKDEIGNRAIDLFETSVKNYQSMAANTIDSLVVGLISPPLQCCGVNNGDD
FTTSPNFWRNDTYGGKTYNNIAYPVVCCKLNQNYAIIDSTCPDQFNENNSNYKTGCRGPL
KELFLKYMDFVAYGLIAAFVILVSIIAFIKIYFELLFFVFN
(SEQ IN NO: 28)
```

Figure 13B

```
ggcacgagag aatgcgttcg atactcgtgt tggtggctct gatcggatgc attgctgcgg
gtgtatataa aatcccattg aaaagaatca ctccgccgat gataaaaatg ttgagagctg
gtacttggga aacgtacgta gaaggaatga ggaagagaca attacagtta ctgaaggagc
acaaggttca tatccaagat gtactcggct atgctaacat ggagtacctc ggcgaaatta
ctattggaac tcctcaacag aagtttctgg tggttttgga cactggctcc tcgaatctgt
gggtccctga tgattcatgc tacaaggaga agagacctga tagatgtcta gtatcaaact
gtgatgctgg actggtttgt caagtcttct gtccagatcc taaatgctgt gaacatacga
gagaattcaa gcaagtaaac gcatgcaaag ataagcatcg atttgatcaa aagaattcca
acacttatgt taaaacaaac aaaacatggg caatagcgta tggaactgga gatgcgaggg
gattttttgg aagagataca gtccgtttgg gtgctgaagg aaaggatcag ctcgttatta
atgatacgtg gttcggacaa gcagagcata tagctgaatt tttcagtaat actttccttg
atggcattct cggactcgct tttcaagaac tgtcagaagg aggcgtcgct cctccaataa
ttcgtgccat tgaccttgga cttctcgatc aaccaatatt tactgtctat ttcgaaaatg
tcggagacaa agaaggtgtt tatggaggtg ttttcacctg gggtggtctc gatccgatc
attgcgaaga tgaggtcaca tatgaacagc taaccgaagc aacttactgg cagtttagac
ttaaaggagt gtcgtctaag aacttctcgt cgacggctgg ttgggaagca atatccgaca
ctggtacctc gttaaatgga gcccctaggg ggatactaag aagtattgca agacagtata
atggacagta cgtcgcatct caaggtctct acgtcgtcga ctgcagtaaa aatgtgaccg
ttgacgtgac cattggcgac agaaactaca ctatgactgc gaaaaatctc gtacttgaaa
tacaggctga tatatgtatt atggcatttt tcgaaatgga catgttcatt ggaccagcat
ggattcttgg cgatccattt attcgagaat attgcaatat tcatgacatt gaaaagaagc
ggattggttt tgcagctgta aacattgat cgattataaa tgtaatgggc tatttgtcat
aaattgctca ataaagtttt ttgactaaaa aaaaaaaaaa aaaaaa (SEQ IN NO: 29)
```

*Figure 14A*

```
MRSILVLVALIGCIAAGVYKIPLKRITPPMIKMLRAGTWETYVEGMRKRQLQLLKEHKVHIQDVL
GYANMEYLGEITIGTPQQKFLVVLDTGSSNLWVPDDSCYKEKRPDRCLVSNCDAGLVCQVFCPDP
KCCEHTREFKQVNACKDKHRFDQKNSNTYVKTNKTWAIAYGTGDARGFFGRDTVRLGAEGKDQLV
INDTWFGQAEHIAEFFSNTFLDGILGLAFQELSEGGVAPPIIRAIDLGLLDQPIFTVYFENVGDK
EGVYGGVFTWGGLDPDHCEDEVTYEQLTEATYWQFRLKGVSSKNFSSTAGWEAISDTGTSLNGAP
RGILRSIARQYNGQYVASQGLYVVDCSKNVTVDVTIGDRNYTMTAKNLVLEIQADICIMAFFEMD
MFIGPAWLLGDPFIREYCNIHDIEKKRIGFAAVKH      (SEQ IN NO: 30)
```

*Figure 14B*

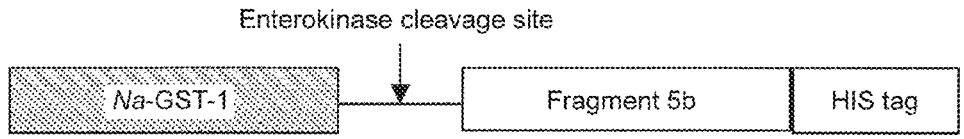

Figure 15A

DNA sequence

ATGGTTCATTACAAGTTAACCTACTTCGCTATACGTGGAGCCGGAGAATGTGCAAGACAGATCTT
CGCACTTGCCGATCAGGAATTCGAGGATGTCCGTTTAGACAAAGAGCAGTTCGCAAAAGTGAAGC
CTGATTTGCCTTTCGGACAGGTTCCAGTCCTTGAAGTCGATGGCAAGCAACTGGCTCAATCCCTT
GCGATTTGCCGCTATCTGGCCAGGCAGTTCGGTTTCGCAGGCAAATCAACGTTCGATGAAGCCGT
AGTCGACTCTTTAGCAGACCAGTATTCTGACTATCGCGTCGAGATCAAGTCGTTCTTCTACACTG
TCATTGGAATGCGAGAAGGTGATGTGGAGCAACTCAAAAAAGAAGTGTTACTTCCTGCTCGCGAT
AAATTCTTCGGATTCATCACTAAATTCCTTAAGAAAAGCCCTTCTGGTTTCCTTGTCGGTGACTC
ACTGACGTGGGTGGACCTCTTGGTCTCGGAGCACAATGCTACAATGCTTACGTTTGTACCAGAGT
TCCTTGAAGGCTATCCTGAAGTAAAAGAGCACATGGAAAAGATACGAGCGATTCCGAAACTGAAG
AAATGGATCGAAACCCGACCAGAGACATTGTTCGGTACCGGTGGTGGCTCCGGTGATGACGACGA
CAAGAGTCCCATGGGTAGGGCGGCAAGCAGCAGCATTGCGTGCCCGAACGGCTGTCAGGCGATTG
CGGATACCGGCACCAGCCTGATTGCGGGTCCGAAAGCGCAGGTGGAAGCGATTCAGAAATATATT
GGCGCGGAACCGCTGATGCTCGAGCACCACCACCACCACCACCACTAA
(SEQ ID NO: 31)

Figure 15B

Amino acid sequence

MVHYKLTYFAIRGAGECARQIFALADQEFEDVRLDKEQFAKVKPDLPFGQVPVLEVDGKQ
LAQSLAICRYLARQFGFAGKSTFDEAVVDSLADQYSDYRVEIKSFFYTVIGMREGDVEQL
KKEVLLPARDKFFGFITKFLKKSPSGFLVGDSLTWVDLLVSEHNATMLTFVPEFLEGYPE
VKEHMEKIRAIPKLKKWIETRPETLFGTGGGSGDDDDKSPMGRAASSSIACPNGCQAIAD
TGTSLIAGPKAQVEAIQKYIGAEPLMLEHHHHHHHH
(SEQ ID NO: 32)

Figure 15C

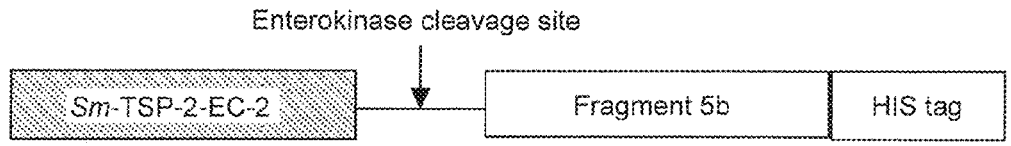

Figure 16A

```
DNA sequence

ATGGAAAAGCCCAAGGTCAAAAAACACATCACTAGTGCATTAAAAAAATTAGT
AGATAAGTACCGTAATGACGAACATGTTCGAAAAGTTTTTGATGAAATCCAAC
AAAAATTACATTGCTGTGGTGCTGACTCTCCTAAAGATTATGGCGAAAATCCA
CCGACATCATGTTCAAAAGATGGCGTACAATTTACAGAGGGATGTATTAAAAA
GGTCAGCGATCTAAGCAAAGCGCACGGTACCGGTGGTGGCTCCGGTGATGACG
ACGACAAGAGTCCCATGGGTAGGGCGGCAAGCAGCAGCATTGCGTGCCCGAAC
GGCTGTCAGGCGATTGCGGATACCGGCACCAGCCTGATTGCGGGTCCGAAAGC
GCAGGTGGAAGCGATTCAGAAATATATTGGCGCGGAACCGCTGATGCTCGAGC
ACCACCACCACCACCACCACTAA
(SEQ ID NO: 33)
```

Figure 16B

```
Amino acid sequence

MEKPKVKKHITSALKKLVDKYRNDEHVRKVFDEIQQKLHCCGADSPKDYGENPP
TSCSKDGVQFTEGCIKKVSDLSKAHGTGGGSGDDDDKSPMGRAASSSIACPNG
CQAIADTGTSLIAGPKAQVEAIQKYIGAEPLMLEHHHHHHHH
(SEQ ID NO: 34)
```

Figure 16C

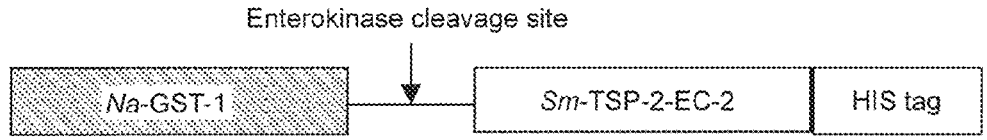

*Figure 17A*

```
DNA sequence

ATGGTTCATTACAAGTTAACCTACTTCGCTATACGTGGAGCCGGAGAATGTGCAAGACAGATCTT
CGCACTTGCCGATCAGGAATTCGAGGATGTCCGTTTAGACAAAGAGCAGTTCGCAAAAGTGAAGC
CTGATTTGCCTTTCGGACAGGTTCCAGTCCTTGAAGTCGATGGCAAGCAACTGGCTCAATCCCTT
GCGATTTGCCGCTATCTGGCCAGGCAGTTCGGTTTCGCAGGCAAATCAACGTTCGATGAAGCCGT
AGTCGACTCTTTAGCAGACCAGTATTCTGACTATCGCGTCGAGATCAAGTCGTTCTTCTACACTG
TCATTGGAATGCGAGAAGGTGATGTGGAGCAACTCAAAAAAGAAGTGTTACTTCCTGCTCGCGAT
AAATTCTTCGGATTCATCACTAAATTCCTTAAGAAAAGCCCTTCTGGTTTCCTTGTCGGTGACTC
ACTGACGTGGGTGGACCTCTTGGTCTCGGAGCACAATGCTACAATGCTTACGTTTGTACCAGAGT
TCCTTGAAGGCTATCCTGAAGTAAAAGAGCACATGGAAAAGATACGAGCGATTCCGAAACTGAAG
AAATGGATCGAAACCCGACCAGAGACATTGTTCGGTACCGGTGGTGGCTCCGGTGATGACGACGA
CAAGAGTCCCATGGGTAGGGCGGCAGAAAAGCCCAAGGTCAAAAAACACATCACTAGTGCATTAA
AAAAATTAGTAGATAAGTACCGTAATGACGAACATGTTCGAAAAGTTTTTGATGAAATCCAACAA
AAATTACATTGCTGTGGTGCTGACTCTCCTAAAGATTATGGCGAAAATCCACCGACATCATGTTC
AAAAGATGGCGTACAATTTACAGAGGGATGTATTAAAAAGGTCAGCGATCTAAGCAAAGCGCACC
TCGAGCACCACCACCACCACCACCACTAA
(SEQ ID NO: 35)
```

*Figure 17B*

```
Amino acid sequence

MVHYKLTYFAIRGAGECARQIFALADQEFEDVRLDKEQFAKVKPDLPFGQVPVLEVDGKQ
LAQSLAICRYLARQFGFAGKSTFDEAVVDSLADQYSDYRVEIKSFFYTVIGMREGDVEQL
KKEVLLPARDKFFGFITKFLKKSPSGFLVGDSLTWVDLLVSEHNATMLTFVPEFLEGYPE
VKEHMEKIRAIPKLKKWIETRPETLFGTGGGSGDDDDKSPMGRAAEKPKVKKHITSALKK
LVDKYRNDEHVRKVFDEIQQKLHCCGADSPKDYGENPPTSCSKDGVQFTEGCIKKVSDLS
KAHLEHHHHHHHH
(SEQ ID NO: 36)
```

*Figure 17C*

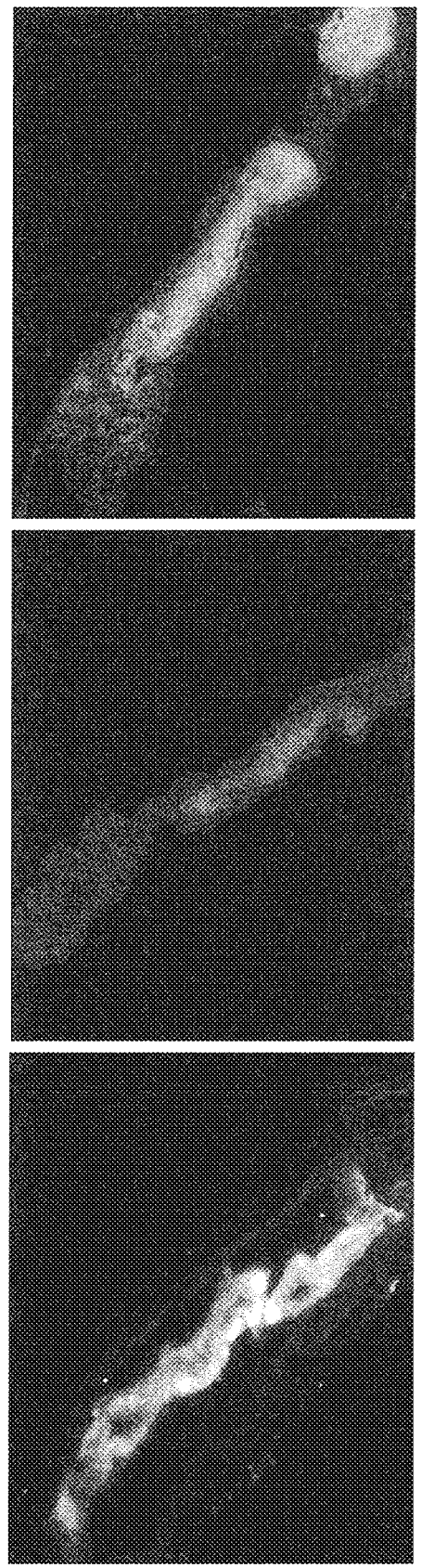
Figure 18A 2H12
Figure 18B 9E10
Figure 18C 11F3

Figure 21

SEQUENCE LISTING

<160> NUMBER OF SEQ ID NOS: 48

<210> SEQ ID NO 1
<211> LENGTH: 753
<212> TYPE: DNA
<213> ORGANISM: Necator americanus

<400> SEQUENCE: 1
gaaaatcaca atgatgtctt ctatcacatg tttggttctt ctctcgattg cagcgtactc      60
caaagccggt tgtcctgaca atggaatgtc agaggaagca cggcaaaaat tccttgaatt     120
gcacaattcg ttgagaagtt cggttgcatt gggacaggcc aaggatggag ctggtggaaa     180

```
tgccccgaaa gctgctaaga tgaagacgat ggcatacgat tgcgaagttg aaaagactgc      240
aatgaataac gcgaaacaat gtgtattcaa gcactcgcaa cctaaccaaa ggaaaggatt      300
gggagagaat atatttatgt cttcggatag cggtatggac aaagcaaagg ctgctgagca      360
ggctagcaaa gcttggttcg gcgaacttgc agaaaaagga gttggacaga atcttaagct      420
tacaggaggc ttgttcagca gaggagtcgg gcactataca cagatggtat ggcaagaaac      480
cgttaagctt ggatgctatg tggaagcgtg ctcaaatatg tgttatgtgg tgtgccagta      540
cggtcctgct ggaaatatga tgggcaagga tatctacgag aaaggagaac cgtgttcgaa      600
atgtgagaat tgcgacaagg agaagggact ctgcagtgct tgattagttg tgttcagtga      660
agctcattac gctcacatac tttaacaaat cgtagtgatc tgtagttgct ttaatattca      720
aataaacatg atgccagcaa aaaaaaaaaa aaa                                   753
```

<210> SEQ ID NO 2
<211> LENGTH: 207
<212> TYPE: PRT
<213> ORGANISM: Necator americanus

<400> SEQUENCE: 2

```
Met Ser Ser Ile Thr Cys Leu Val Leu Leu Ser Ile Ala Ala Tyr Ser
1               5                   10                  15

Lys Ala Gly Cys Pro Asp Asn Gly Met Ser Glu Glu Ala Arg Gln Lys
            20                  25                  30

Phe Leu Glu Leu His Asn Ser Leu Arg Ser Ser Val Ala Leu Gly Gln
        35                  40                  45

Ala Lys Asp Gly Ala Gly Gly Asn Ala Pro Lys Ala Ala Lys Met Lys
    50                  55                  60

Thr Met Ala Tyr Asp Cys Glu Val Glu Lys Thr Ala Met Asn Asn Ala
65                  70                  75                  80

Lys Gln Cys Val Phe Lys His Ser Gln Pro Asn Gln Arg Lys Gly Leu
                85                  90                  95

Gly Glu Asn Ile Phe Met Ser Ser Asp Ser Gly Lys Ala Lys Ala Ala
            100                 105                 110

Glu Gln Ala Ser Lys Ala Trp Phe Gly Glu Leu Ala Glu Lys Gly Val
        115                 120                 125

Gly Gln Asn Leu Lys Leu Thr Gly Gly Leu Phe Ser Arg Gly Val Gly
    130                 135                 140

His Tyr Thr Gln Met Val Trp Gln Glu Thr Val Lys Leu Gly Cys Tyr
145                 150                 155                 160

Val Glu Ala Cys Ser Asn Met Cys Tyr Val Val Cys Gln Tyr Gly Pro
                165                 170                 175

Ala Gly Asn Met Met Gly Lys Asp Ile Tyr Glu Lys Gly Glu Pro Cys
            180                 185                 190

Ser Lys Cys Glu Asn Cys Asp Lys Glu Lys Gly Leu Cys Ser Ala
        195                 200                 205
```

<210> SEQ ID NO 3
<211> LENGTH: 527
<212> TYPE: DNA
<213> ORGANISM: Necator americanus

<400> SEQUENCE: 3

```
aaaagcctcc atagtcatgc tcaagctcgt tgcactcgtt tgcctggttg caatctgctt      60
cgctcaggga ccacaaggac cccctccgtt cctgcaaagt gctccagcgg ctgttcaaca     120
agacttcgac aagctcttcg tcaatgctgg ctccaagact gatgcagaaa tcgacaaaat     180
```

| ggtccaagat tgggttggca aacaagatgc atccatcaag accgcattcg atgcgttcgt | 240 |
| --- | --- |
| gaaggaagtg aaagccgctc aagcgcaagg tgaagctgcc catcaggctg ctatcgccaa | 300 |
| gttcagcgca gaggccaaag cggctgatgc caagctgagc gcaattgcga acgacaggtc | 360 |
| gaagacaaac gcgcaaaagg gagctgagat cgactcggta ctcaagggac ttcctccaaa | 420 |
| tgtccgcaca gagatcgaaa acgccatgaa aggataagaa gtctctattt tgtatatatg | 480 |
| aaccgataaa tatgcacaat aaaaaaaaaa aaaaaaaaaa aaaaaaa | 527 |

<210> SEQ ID NO 4
<211> LENGTH: 146
<212> TYPE: PRT
<213> ORGANISM: Necator americanus

<400> SEQUENCE: 4

Met Leu Lys Leu Val Ala Leu Val Cys Leu Val Ala Ile Cys Phe Ala
1               5                   10                  15

Gln Gly Pro Gln Gly Pro Pro Phe Leu Gln Ser Ala Pro Ala Ala
            20                  25                  30

Val Gln Gln Asp Phe Asp Lys Leu Phe Val Asn Ala Gly Ser Lys Thr
        35                  40                  45

Asp Ala Glu Ile Asp Lys Met Val Gln Asp Trp Val Gly Lys Gln Asp
    50                  55                  60

Ala Ser Ile Lys Thr Ala Phe Asp Ala Phe Val Lys Glu Val Lys Ala
65                  70                  75                  80

Ala Gln Ala Gln Gly Glu Ala Ala His Gln Ala Ala Ile Ala Lys Phe
                85                  90                  95

Ser Ala Glu Ala Lys Ala Ala Asp Ala Lys Leu Ser Ala Ile Ala Asn
            100                 105                 110

Asp Arg Ser Lys Thr Asn Ala Gln Lys Gly Ala Glu Ile Asp Ser Val
        115                 120                 125

Leu Lys Gly Leu Pro Pro Asn Val Arg Thr Glu Ile Glu Asn Ala Met
    130                 135                 140

Lys Gly
145

<210> SEQ ID NO 5
<211> LENGTH: 1293
<212> TYPE: DNA
<213> ORGANISM: Necator americanus

<400> SEQUENCE: 5

| agcgttcatc gacgactctt tcatcaagct cgtcgtcatg tgacatcggt atcgctttcg | 60 |
| --- | --- |
| cgtcagccaa cacttcgtga acgactgatc gcaagtggca gttgggagga ttaccagaaa | 120 |
| caacgctacc attatcaaaa gaaaattcta gcaaaatatg ctgctaacaa agcgtcaaag | 180 |
| ttacaatctg caaacgagat cgatgaattg ctccggaact atatggatgc acaatactat | 240 |
| ggtgtcatcc aaattgggac tccagctcag aatttcactg tgatcttcga cacgggttcc | 300 |
| tcaaatctat gggtaccgtc aagaaagtgt ccattctatg acattgcatg tatgcttcat | 360 |
| catcgttatg actccggagc ctcgtcaacc tgcaaggaag atgggcgcaa gatggctatt | 420 |
| cagtatggaa ctggatctat gaaaggattc atttctaagg atattgtttg tattgctgga | 480 |
| atttgcgctg aagaacaacc tttcgcggag gctacaagtg aacctggtct tacatttatc | 540 |
| gctgctaagt tgatggaat ccttggaatg gcattcccgg aaattgctgt ctcggtgta | 600 |
| actcctgtct tccatacgtt cattgaacag aagaaagttc ctagccctgt gtttgctttc | 660 |

```
tggccgaata ggaatccaga gtcggaaatt ggaggagaga ttacctttgg tggtgtggat    720
acccgacgtt atgttgaacc aattacatgg acaccagtga cacgtcgtgg atattggcaa    780
ttcaaaatgg atatggtaca aggtggttca tcgtccattg cgtgtccgaa tggatgccaa    840
gctatcgctg atactggcac ttctcttatt gctggaccga aggcacaggt tgaggcaatc    900
cagaaatata tcggagcaga gccgcttatg aaaggagaat acatgattcc ttgcgacaaa    960
gtaccatccc ttcctgatgt ttcgttcatc atcgatggca agacgtttac actcaaaggg   1020
gaagattacg ttctaaccgt gaaagccgct ggtaaatcaa tctgtttgtc tggcttcatg   1080
ggaatggact cccagagaa gatcggcgaa ttgtggatcc ttggagatgt tttcattgga   1140
aaatactaca ccgtcttcga tgttggtcag gcacgtgttg gatttgctca agcaaagtca   1200
gaagatggat tccctgttgg accccccgtt cgaacattca cagcttca ggaagacagc    1260 gatagcgacg aggacgatgt atttactttt taa                                1293
```

<210> SEQ ID NO 6
<211> LENGTH: 430
<212> TYPE: PRT
<213> ORGANISM: Necator americanus
<400> SEQUENCE: 6

```
Ser Val His Arg Arg Leu Phe His Gln Ala Arg Arg His Val Thr Ser
1               5                   10                  15

Val Ser Leu Ser Arg Gln Pro Thr Leu Arg Glu Arg Leu Ile Ala Ser
            20                  25                  30

Gly Ser Trp Glu Asp Tyr Gln Lys Gln Arg Tyr His Tyr Gln Lys Lys
        35                  40                  45

Ile Leu Ala Lys Tyr Ala Ala Asn Lys Ala Ser Lys Leu Gln Ser Ala
    50                  55                  60

Asn Glu Ile Asp Glu Leu Leu Arg Asn Tyr Met Asp Ala Gln Tyr Tyr
65                  70                  75                  80

Gly Val Ile Gln Ile Gly Thr Pro Ala Gln Asn Phe Thr Val Ile Phe
                85                  90                  95

Asp Thr Gly Ser Ser Asn Leu Trp Val Pro Ser Arg Lys Cys Pro Phe
            100                 105                 110

Tyr Asp Ile Ala Cys Met Leu His His Arg Tyr Asp Ser Gly Ala Ser
        115                 120                 125

Ser Thr Cys Lys Glu Asp Gly Arg Lys Met Ala Ile Gln Tyr Gly Thr
    130                 135                 140

Gly Ser Met Lys Gly Phe Ile Ser Lys Asp Ile Val Cys Ile Ala Gly
145                 150                 155                 160

Ile Cys Ala Glu Glu Gln Pro Phe Ala Glu Ala Thr Ser Glu Pro Gly
                165                 170                 175

Leu Thr Phe Ile Ala Ala Lys Phe Asp Gly Ile Leu Gly Met Ala Phe
            180                 185                 190

Pro Glu Ile Ala Val Leu Gly Val Thr Pro Val Phe His Thr Phe Ile
        195                 200                 205

Glu Gln Lys Lys Val Pro Ser Pro Val Phe Ala Phe Trp Pro Asn Arg
    210                 215                 220

Asn Pro Glu Ser Glu Ile Gly Gly Glu Ile Thr Phe Gly Gly Val Asp
225                 230                 235                 240

Thr Arg Arg Tyr Val Glu Pro Ile Thr Trp Thr Pro Val Thr Arg Arg
                245                 250                 255

Gly Tyr Trp Gln Phe Lys Met Asp Met Val Gln Gly Gly Ser Ser Ser
```

```
                     260                 265                 270
Ile Ala Cys Pro Asn Gly Cys Gln Ala Ile Ala Asp Thr Gly Thr Ser
            275                 280                 285

Leu Ile Ala Gly Pro Lys Ala Gln Val Glu Ala Ile Gln Lys Tyr Ile
        290                 295                 300

Gly Ala Glu Pro Leu Met Lys Gly Glu Tyr Met Ile Pro Cys Asp Lys
305                 310                 315                 320

Val Pro Ser Leu Pro Asp Val Ser Phe Ile Ile Asp Gly Lys Thr Phe
                325                 330                 335

Thr Leu Lys Gly Glu Asp Tyr Val Leu Thr Val Lys Ala Ala Gly Lys
            340                 345                 350

Ser Ile Cys Leu Ser Gly Phe Met Gly Met Asp Phe Pro Glu Lys Ile
        355                 360                 365

Gly Glu Leu Trp Ile Leu Gly Asp Val Phe Ile Gly Lys Tyr Tyr Thr
370                 375                 380

Val Phe Asp Val Gly Gln Ala Arg Val Gly Phe Ala Gln Ala Lys Ser
385                 390                 395                 400

Glu Asp Gly Phe Pro Val Gly Thr Pro Val Arg Thr Phe Arg Gln Leu
                405                 410                 415

Gln Glu Asp Ser Asp Ser Asp Glu Asp Asp Val Phe Thr Phe
            420                 425                 430

<210> SEQ ID NO 7
<211> LENGTH: 1441
<212> TYPE: DNA
<213> ORGANISM: Necator americanus

<400> SEQUENCE: 7
ggcacgaggg gagatggctc gacttgtatt cctactcgta ctatgtactc tggctgcaca     60
agcgttcatc gacgactctt tcatcaagct cgtcgtcatg tgacatcggt atcgctttcg    120
cgtcagccaa cacttcgtga acgactgatc gcaagtggca gttgggagga ttaccagaaa    180
caacgctacc attatcgaaa gaaaattcta gcaaaatatg ctgctaacaa agcgtcaaag    240
ttacaatctg caaacgagat cgatgaattg ctccggaact atatggatgc acaatactat    300
ggtgtcatcc aaattgggac tccagctcag aatttcactg tgatcttcga cacgggttcc    360
tcaaatctat gggtaccgtc aagaaagtgt ccattctatg acattgcatg tatgcttcat    420
catcgttatg actccggagc ctcgtcaacc tacaaggaag atgggcgcaa gatggctatt    480
cagtatggaa ctggatctat gaaggattca atttctaagg atattgtttg tattgctgga    540
atttgcgctg aagaacaacc tttcgcggag gctacaagtg aacctggtct tacatttatc    600
gctgctaagt tgatggaat ccttggaatg gcattcccgg aaattgctgt ctcggtgta    660 actcctgtct ccatacgtt cattgaacag aagaaagttc ctagccctgt gtttgctttc    720
tggctgaata ggaatccaga gtcggaaatt ggaggagaga ttacctttgg tggtgtggat    780
acccgacgtt atgttgaacc aattacatgg acaccagtga cacgtcgtgg atattggcaa    840
ttcaaaatgg atatggtaca aggtggttca tcgtccattg cgtgtccgaa tggatgccaa    900
gctatcgctg atactggcac ttctcttatt gctggaccga aggcacaggt tgaggcaatc    960
cagaaatata tcggagcaga gccgcttatg aaaggagaat acatgattcc ttgcgacaaa   1020
gtaccatccc ttcctgatgt ttcgttcatc atcgatggca agacgtttac actcaaaggg   1080
gaagattacg ttctaaccgt gaaagccgct ggtaaatcaa tctgtttgtc tggcttcatg   1140
ggaatggact tcccagagaa gatcggcgaa ttgtggatcc ttggagatgt tttcattgga   1200
```

```
aaatactaca ccgtcttcga tgttggtcag gcacgtgttg gatttgctca agcaaagtca    1260
gaagatggat tccctgttgg caccccgtt cgaacattca gacagcttca ggaagacagc    1320
gatagcgacg aggacgatgt atttactttt aagtagtgt taacatctcc aacgtgctct    1380
gttacttcta cgtgtaccat gtttcacgtg tttgctcatt tgataaatta ttatcttccc    1440
t                                                                    1441
```

<210> SEQ ID NO 8
<211> LENGTH: 446
<212> TYPE: PRT
<213> ORGANISM: Necator americanus

<400> SEQUENCE: 8

```
Met Ala Arg Leu Val Phe Leu Val Leu Cys Thr Leu Ala Ala Ala
1               5                   10                  15

Ser Val His Arg Arg Leu Phe His Gln Ala Arg Arg His Val Thr Ser
            20                  25                  30

Val Ser Leu Ser Arg Gln Pro Thr Leu Arg Glu Arg Leu Ile Ala Ser
        35                  40                  45

Gly Ser Trp Glu Asp Tyr Gln Lys Gln Arg Tyr His Tyr Arg Lys Lys
    50                  55                  60

Ile Leu Ala Lys Tyr Ala Ala Asn Lys Ala Ser Lys Leu Gln Ser Ala
65                  70                  75                  80

Asn Glu Ile Asp Glu Leu Leu Arg Asn Tyr Met Asp Ala Gln Tyr Tyr
                85                  90                  95

Gly Val Ile Gln Ile Gly Thr Pro Ala Gln Asn Phe Thr Val Ile Phe
            100                 105                 110

Asp Thr Gly Ser Ser Asn Leu Trp Val Pro Ser Arg Lys Cys Pro Phe
        115                 120                 125

Tyr Asp Ile Ala Cys Met Leu His His Arg Tyr Asp Ser Gly Ala Ser
    130                 135                 140

Ser Thr Tyr Lys Glu Asp Gly Arg Lys Met Ala Ile Gln Tyr Gly Thr
145                 150                 155                 160

Gly Ser Met Lys Gly Phe Ile Ser Lys Asp Ile Val Cys Ile Ala Gly
                165                 170                 175

Ile Cys Ala Glu Glu Gln Pro Phe Ala Glu Ala Thr Ser Glu Pro Gly
            180                 185                 190

Leu Thr Phe Ile Ala Ala Lys Phe Asp Gly Ile Leu Gly Met Ala Phe
        195                 200                 205

Pro Glu Ile Ala Val Leu Gly Val Thr Pro Val Phe His Thr Phe Ile
    210                 215                 220

Glu Gln Lys Lys Val Pro Ser Pro Val Phe Ala Phe Trp Leu Asn Arg
225                 230                 235                 240

Asn Pro Glu Ser Glu Ile Gly Gly Glu Ile Thr Phe Gly Gly Val Asp
                245                 250                 255

Thr Arg Arg Tyr Val Glu Pro Ile Thr Trp Thr Pro Val Thr Arg Arg
            260                 265                 270

Gly Tyr Trp Gln Phe Lys Met Asp Met Val Gln Gly Gly Ser Ser Ser
        275                 280                 285

Ile Ala Cys Pro Asn Gly Cys Gln Ala Ile Ala Asp Thr Gly Thr Ser
    290                 295                 300

Leu Ile Ala Gly Pro Lys Ala Gln Val Glu Ala Ile Gln Lys Tyr Ile
305                 310                 315                 320

Gly Ala Glu Pro Leu Met Lys Gly Glu Tyr Met Ile Pro Cys Asp Lys
                325                 330                 335
```

Val Pro Ser Leu Pro Asp Val Ser Phe Ile Ile Asp Gly Lys Thr Phe
            340                 345                 350

Thr Leu Lys Gly Glu Asp Tyr Val Leu Thr Val Lys Ala Ala Gly Lys
            355                 360                 365

Ser Ile Cys Leu Ser Gly Phe Met Gly Met Asp Phe Pro Glu Lys Ile
        370                 375                 380

Gly Glu Leu Trp Ile Leu Gly Asp Val Phe Ile Gly Lys Tyr Tyr Thr
385                 390                 395                 400

Val Phe Asp Val Gly Gln Ala Arg Val Gly Phe Ala Gln Ala Lys Ser
                405                 410                 415

Glu Asp Gly Phe Pro Val Gly Thr Pro Val Arg Thr Phe Arg Gln Leu
            420                 425                 430

Gln Glu Asp Ser Asp Ser Asp Glu Asp Asp Val Phe Thr Phe
        435                 440                 445

<210> SEQ ID NO 9
<211> LENGTH: 1134
<212> TYPE: DNA
<213> ORGANISM: Necator americanus

<400> SEQUENCE: 9
gttaaagccg tgtaagcaac agggttcttt gtgatgttaa ctctcgctgc acttctgatt      60
tctgtttcgc tggttgagcc gacaggcata ggtgagtttc ttgctcaacc agcacctgca     120
tatgctagaa gactcacagg gcaggcccct gttgactacg tcaattcgca ccactcattg     180
tacaaggcca atattcacc agatgctcaa gaacgcatga atctagaat tatggatttg       240 agtttcatgg ttgatgcgga agtcatgatg gaagaaatgg accagcagga ggatatagat    300
ctcgctgttt ctttacctga aagtttcgac gctcgtgaaa atggccaga atgtccttca     360 ataggattaa tccgtgatca gtccgccggt ggaggatgtt gggcagtatc ctcagcagag    420
gtgatgaccg acaggatctg tatacaatca atggaacaa agcaggtgta tgtttccgaa     480
acggatatct tatcatgctg tggacaacgt tgcggtagcg ggtgtacctc aggtgtgcca    540
cgtcaagctt tcaactatgc aattcgtaaa ggtgtttgca gtggaggacc atatggaacg    600
aagggtgttt gcaaacccta tcctttctat ccatgcggct atcatgctca tctgccatat    660 tatgaccat gtccagatgg tatgtggcct acgccaacat gcgaaaaggc atgtcaatcc     720
gactatactg ttccgtacaa cgatgacagg atcttcggca gcaaaactat tgtcttgacg    780
ggagaggaaa aaattaagcg agagattttc aataacggac cattggtagc cacgtataca    840
gtttacgaag atttcgctta ttacaagaat ggaatttaca tgactggtct cggtagagcg    900
acaggcgcac atgcagtcaa aattattggc tggggtgaag aaaatggagt caagtattgg    960
ttgattgcaa actcgtggaa cactgattgg ggagagaatg gcttcttccg catgcttcgt   1020
ggaacaaacc tttgcgatat tgaactaagc gcgactggag aacgttcaa ggtgtgaacg     1080 tgatcgaaaa gaacgatttt gaacaaaaat cttcccgtat tgtcatcaaa aaaa          1134

<210> SEQ ID NO 10
<211> LENGTH: 347
<212> TYPE: PRT
<213> ORGANISM: Necator americanus

<400> SEQUENCE: 10

Met Leu Thr Leu Ala Ala Leu Leu Ile Ser Val Ser Leu Val Glu Pro
1               5                   10                  15

Thr Gly Ile Gly Glu Phe Leu Ala Gln Pro Ala Pro Ala Tyr Ala Arg

```
                    20                  25                  30
Arg Leu Thr Gly Gln Ala Leu Val Asp Tyr Val Asn Ser His His Ser
            35                  40                  45
Leu Tyr Lys Ala Lys Tyr Ser Pro Asp Ala Gln Glu Arg Met Lys Ser
        50                  55                  60
Arg Ile Met Asp Leu Ser Phe Met Val Asp Ala Glu Val Met Met Glu
65                  70                  75                  80
Glu Met Asp Gln Gln Glu Asp Ile Asp Leu Ala Val Ser Leu Pro Glu
                85                  90                  95
Ser Phe Asp Ala Arg Glu Lys Trp Pro Glu Cys Pro Ser Ile Gly Leu
            100                 105                 110
Ile Arg Asp Gln Ser Ala Gly Gly Cys Trp Ala Val Ser Ser Ala
        115                 120                 125
Glu Val Met Thr Asp Arg Ile Cys Ile Gln Ser Asn Gly Thr Lys Gln
    130                 135                 140
Val Tyr Val Ser Glu Thr Asp Ile Leu Ser Cys Cys Gly Gln Arg Cys
145                 150                 155                 160
Gly Ser Gly Cys Thr Ser Gly Val Pro Arg Gln Ala Phe Asn Tyr Ala
                165                 170                 175
Ile Arg Lys Gly Val Cys Ser Gly Gly Pro Tyr Gly Thr Lys Gly Val
            180                 185                 190
Cys Lys Pro Tyr Pro Phe Tyr Pro Cys Gly Tyr His Ala His Leu Pro
        195                 200                 205
Tyr Tyr Gly Pro Cys Pro Asp Gly Met Trp Pro Thr Pro Thr Cys Glu
    210                 215                 220
Lys Ala Cys Gln Ser Asp Tyr Thr Val Pro Tyr Asn Asp Asp Arg Ile
225                 230                 235                 240
Phe Gly Ser Lys Thr Ile Val Leu Thr Gly Glu Lys Ile Lys Arg
                245                 250                 255
Glu Ile Phe Asn Asn Gly Pro Leu Val Ala Thr Tyr Thr Val Tyr Glu
            260                 265                 270
Asp Phe Ala Tyr Tyr Lys Asn Gly Ile Tyr Met Thr Gly Leu Gly Arg
        275                 280                 285
Ala Thr Gly Ala His Ala Val Lys Ile Ile Gly Trp Gly Glu Glu Asn
    290                 295                 300
Gly Val Lys Tyr Trp Leu Ile Ala Asn Ser Trp Asn Thr Asp Trp Gly
305                 310                 315                 320
Glu Asn Gly Phe Phe Arg Met Leu Arg Gly Thr Asn Leu Cys Asp Ile
                325                 330                 335
Glu Leu Ser Ala Thr Gly Gly Thr Phe Lys Val
            340                 345

<210> SEQ ID NO 11
<211> LENGTH: 1177
<212> TYPE: DNA
<213> ORGANISM: Necator americanus

<400> SEQUENCE: 11
ttaattctta ttgctctggt ggtgacggcg ttggctcaac agccgctttc actaaaggag    60
tatctggaac agccgatacc agaggaggca gagaatcttt ccggagaagc gtttgcggag   120
tttctgaaca aacgacaatc gttttcacg gctaagtaca cgccaaatgc tttaaacatt    180
cttaaaatgc gtgtgatgga atcgagattc ctggacaatg aagaaggtga atgctaaaa    240 gaggaggaca tggatttcag tgaagaaatt cctgttagtt ttgatgctcg agacaaatgg   300
```

-continued

| | |
|---|---|
| cccaaatgca cctccatagg atttatccgt gatcaatcac actgtggttc atgctgggca | 360 |
| gtatcgtcag cagaaacgat gtcagatcga ctctgcgtgc aatcaaacgg tacaattaag | 420 |
| gtacttctat ccgatacgga catccttgcc tgttgcccga attgtggtgc tggatgtgga | 480 |
| ggaggccaca caattcgagc gtgggaatat tttaagaaca caggcgtttg cactggcgga | 540 |
| ctatatggaa caaggattc ctgcaaacca tacgctttct atccatgtaa agacgaaagt | 600 |
| tacgaaagt gccccaagga ttcttttcca acaccaaaat gtcgaaaaat ttgtcagtat | 660 |
| aaatacagta agaagtacgc cgacgacaaa tactacgcga attccgcata tcgaattcca | 720 |
| cagaatgaga cgtggatcaa attggagatc atgagaaacg ggcctgtgac agcatcattc | 780 |
| aggatttatc cggattttgg gttttacgaa aaaggagttt atgtgacttc aggcggaagg | 840 |
| gaactaggtg ggcacgcgat taaaatcatt ggatggggaa cggaaaaagt aaacggaact | 900 |
| gacctacctt actggttgat tgctaactct tggggtactg actggggaga gaataacggc | 960 |
| tatttccgca tacttcgcgg acaaaatcac tgccaaatag aacagaaagt tatcgccggt | 1020 |
| atgataaaag taccacaacc gaaatccgcc ggtccaccac ttcaacccaa tccttcaagc | 1080 |
| tgaaccaagt tgtagtattg tccccatcaa tccaagcatt tcttggggtg atacttttac | 1140 |
| gaataaaaac tacattataa aaaaaaaaaa aaaaaaa | 1177 |

<210> SEQ ID NO 12
<211> LENGTH: 360
<212> TYPE: PRT
<213> ORGANISM: Necator americanus

<400> SEQUENCE: 12

Leu Ile Leu Ile Ala Leu Val Val Thr Ala Leu Ala Gln Gln Pro Leu
1               5                   10                  15

Ser Leu Lys Glu Tyr Leu Glu Gln Pro Ile Pro Glu Glu Ala Glu Asn
        20                  25                  30

Leu Ser Gly Glu Ala Phe Ala Glu Phe Leu Asn Lys Arg Gln Ser Phe
    35                  40                  45

Phe Thr Ala Lys Tyr Thr Pro Asn Ala Leu Asn Ile Leu Lys Met Arg
50                  55                  60

Val Met Glu Ser Arg Phe Leu Asp Asn Glu Glu Gly Glu Met Leu Lys
65                  70                  75                  80

Glu Glu Asp Met Asp Phe Ser Glu Glu Ile Pro Val Ser Phe Asp Ala
                85                  90                  95

Arg Asp Lys Trp Pro Lys Cys Thr Ser Ile Gly Phe Ile Arg Asp Gln
            100                 105                 110

Ser His Cys Gly Ser Cys Trp Ala Val Ser Ser Ala Glu Thr Met Ser
        115                 120                 125

Asp Arg Leu Cys Val Gln Ser Asn Gly Thr Ile Lys Val Leu Leu Ser
    130                 135                 140

Asp Thr Asp Ile Leu Ala Cys Cys Pro Asn Cys Gly Ala Gly Cys Gly
145                 150                 155                 160

Gly Gly His Thr Ile Arg Ala Trp Glu Tyr Phe Lys Asn Thr Gly Val
                165                 170                 175

Cys Thr Gly Gly Leu Tyr Gly Thr Lys Asp Ser Cys Lys Pro Tyr Ala
            180                 185                 190

Phe Tyr Pro Cys Lys Asp Glu Ser Tyr Gly Lys Cys Pro Lys Asp Ser
        195                 200                 205

Phe Pro Thr Pro Lys Cys Arg Lys Ile Cys Gln Tyr Lys Tyr Ser Lys
    210                 215                 220

```
Lys Tyr Ala Asp Asp Lys Tyr Ala Asn Ser Ala Tyr Arg Ile Pro
225                 230                 235                 240

Gln Asn Glu Thr Trp Ile Lys Leu Glu Ile Met Arg Asn Gly Pro Val
            245                 250                 255

Thr Ala Ser Phe Arg Ile Tyr Pro Asp Phe Gly Phe Tyr Glu Lys Gly
            260                 265                 270

Val Tyr Val Thr Ser Gly Gly Arg Glu Leu Gly Gly His Ala Ile Lys
            275                 280                 285

Ile Ile Gly Trp Gly Thr Glu Lys Val Asn Gly Thr Asp Leu Pro Tyr
290                 295                 300

Trp Leu Ile Ala Asn Ser Trp Gly Thr Asp Trp Gly Glu Asn Asn Gly
305                 310                 315                 320

Tyr Phe Arg Ile Leu Arg Gly Gln Asn His Cys Gln Ile Glu Gln Lys
                325                 330                 335

Val Ile Ala Gly Met Ile Lys Val Pro Gln Pro Lys Ser Ala Gly Pro
            340                 345                 350

Pro Leu Gln Pro Asn Pro Ser Ser
            355                 360

<210> SEQ ID NO 13
<211> LENGTH: 1181
<212> TYPE: DNA
<213> ORGANISM: Necator americanus

<400> SEQUENCE: 13
tcgttgaggc gttatttcaa gcttctctcg cctcgatttc agattctcca attgtttcag      60
tgaatcgtgg aacagtcaat ctcacttttg tgagatccaa tgaaagctaa ttttgcgttg     120
gtcgtcgtcc ttctggcaat aaaccagtta tatgcagatg agctgcttca caaacaagag     180
tccgaacacg gacttagtgg ccaagcgctc gttgactacg ttaattcgca ccaatcactt     240
ttcaaaacag aatattcgcc aaccaatgaa caattcgtta aagcccgtat aatggacata     300
aagtatatga ctgaggctag ccacaaatat ccaagaaagg cattaatctc gaacgttgaa     360
ctccctgaaa ggtttgacgc acgtgaaaaa tggccacatt gcgcctccat cggtctcatt     420
cgcgatcact ctgcttgcgg atcgtgttgg gctgtatcgg cagcgtcggt tatgtcagat     480
cgactctgta tccagacgaa cggcacaaac cagaagatcc tttcgtcggc ggacatcctt     540
gcgtgttgtg agaagactg tggctcagga tgcgaaggcg gttatccgat tcaggcgtac     600
ttctacctgg aaaatactgg agtatgtagt ggaggagagt atcgagaaaa gaatgtatgc     660
aaaccatatc cctttatcc gtgtgacgga aactatggac catgccccaa ggagggtgcg     720
ttcgacactc caaagtgtcg gaaaatatgt cagttccgat atcctgttcc atacgaagaa     780
gataaagtgt ttggaaaaaa ttcacacatc cttctgcaag acaacgaggc aagaatcaga     840
caggaaattt tcataaacgg accagtggga gctaattttt acgttttcga agactttata     900
cactacaagg aagggattta taagcagaca tatgggaaat ggataggagt acatgcaatc     960
aaacttattg gttggggcac agaaaatgga acagattatt ggttggttgc taactcgtac    1020
aactacgact ggggagagaa tggcaccttc cgcattcttc gtggaactaa tcactgtttg    1080
atagaatcac aagtgatcgc aacggagatg attgtatgaa tgtctaatga acgattggtc    1140
gcatgccgat ctctgaagta aatgtgttaa atcaaaaaaa a                        1181

<210> SEQ ID NO 14
<211> LENGTH: 339
<212> TYPE: PRT
<213> ORGANISM: Necator americanus
```

<400> SEQUENCE: 14

```
Met Lys Ala Asn Phe Ala Leu Val Val Leu Leu Ala Ile Asn Gln
1               5                   10                  15

Leu Tyr Ala Asp Glu Leu Leu His Lys Gln Glu Ser Glu His Gly Leu
            20                  25                  30

Ser Gly Gln Ala Leu Val Asp Tyr Val Asn Ser His Gln Ser Leu Phe
        35                  40                  45

Lys Thr Glu Tyr Ser Pro Thr Asn Glu Gln Phe Val Lys Ala Arg Ile
    50                  55                  60

Met Asp Ile Lys Tyr Met Thr Glu Ala Ser His Lys Tyr Pro Arg Lys
65                  70                  75                  80

Gly Ile Asn Leu Asn Val Glu Leu Pro Glu Arg Phe Asp Ala Arg Glu
                85                  90                  95

Lys Trp Pro His Cys Ala Ser Ile Gly Leu Ile Arg Asp His Ser Ala
            100                 105                 110

Cys Gly Ser Cys Trp Ala Val Ser Ala Ala Ser Val Met Ser Asp Arg
        115                 120                 125

Leu Cys Ile Gln Thr Asn Gly Thr Asn Gln Lys Ile Leu Ser Ser Ala
    130                 135                 140

Asp Ile Leu Ala Cys Cys Gly Glu Asp Cys Gly Ser Gly Cys Glu Gly
145                 150                 155                 160

Gly Tyr Pro Ile Gln Ala Tyr Phe Tyr Leu Glu Asn Thr Gly Val Cys
                165                 170                 175

Ser Gly Gly Glu Tyr Arg Glu Lys Asn Val Cys Lys Pro Tyr Pro Phe
            180                 185                 190

Tyr Pro Cys Asp Gly Asn Tyr Gly Pro Cys Pro Lys Glu Gly Ala Phe
        195                 200                 205

Asp Thr Pro Lys Cys Arg Lys Ile Cys Gln Phe Arg Tyr Pro Val Pro
    210                 215                 220

Tyr Glu Glu Asp Lys Val Phe Gly Lys Asn Ser His Ile Leu Leu Gln
225                 230                 235                 240

Asp Asn Glu Ala Arg Ile Arg Gln Glu Ile Phe Ile Asn Gly Pro Val
                245                 250                 255

Gly Ala Asn Phe Tyr Val Phe Glu Asp Phe Ile His Tyr Lys Glu Gly
            260                 265                 270

Ile Tyr Lys Gln Thr Tyr Gly Lys Trp Ile Gly Val His Ala Ile Lys
        275                 280                 285

Leu Ile Gly Trp Gly Thr Glu Asn Gly Thr Asp Tyr Trp Leu Val Ala
    290                 295                 300

Asn Ser Tyr Asn Tyr Asp Trp Gly Glu Asn Gly Thr Phe Arg Ile Leu
305                 310                 315                 320

Arg Gly Thr Asn His Cys Leu Ile Glu Ser Gln Val Ile Ala Thr Glu
                325                 330                 335

Met Ile Val
```

<210> SEQ ID NO 15
<211> LENGTH: 1236
<212> TYPE: DNA
<213> ORGANISM: Necator americanus

<400> SEQUENCE: 15

```
tagataataa tcttttttgca cgtcagagaa tttctttgat aaaaccacaa ttaaacaatc    60
tcagcgctgt aaacacgtgc aaaactactc gttcatttct cttcactttc cctccaaaac   120
```

-continued

| | |
|---|---|
| caaacattca agagaagcat gataaccatc attaccctat tgcttatcgc ttctacagtg | 180 |
| aagtcactaa cagtggagga gtacttggcc cgaccagtgc cggaatatgc acaaaactg | 240 |
| acaggacaag cctacgttga ctatgttaat cagcatcaat cattctacaa ggctgaatat | 300 |
| tccccgctgg ttgaacagta tgccaaagct gtgatgagat ctgagtttat gacgaagccg | 360 |
| aaccaaaatt atgtggtgaa ggacgtagat ctaaacatca atcttccaga aaccttcgac | 420 |
| gcaagggaaa atggccaaa ctgcacatca ataaggacaa ttcgcgatca gtccaattgt | 480 |
| ggatcatgtt gggcagtatc agcggcgtcg gtaatgtcag atcgtttatg catacagtcg | 540 |
| aacggcacaa tacagtcatg ggcttctgat acggatattc tatcatgttg ctggaattgc | 600 |
| ggaatgggat gcgatggagg tagaccgttt gcggcgttct ttttcgcgat agacaatggt | 660 |
| gtatgcactg gaggaccttt cagagagcca acgtgtgca aaccatacgc tttctatcca | 720 |
| tgcggtcgcc accaaaacca gaaatacttc ggaccttgtc caaagagct ctggcccact | 780 |
| ccaaaatgtc ggaaaatgtg tcaactaaaa tataatgtgg cctacaaaga cgataaaatt | 840 |
| tacgggaatg atgcatacag tctccctaac aatgagacac gaatcatgca agaaattttc | 900 |
| acaaatggac ctgtagtggg atcattcagc gtgtttgctg actttgcaat ttataagaaa | 960 |
| ggagtatatg tgagtaatgg aattcagcag aatgggctc atgcagtcaa aattattggt | 1020 |
| tggggtgtgc aggatggact aaaatattgg ttgattgcta attcctggaa caatgactgg | 1080 |
| ggagacgaag gctatgtccg gttccttcgt ggagataacc actgtggaat tgaatcaagg | 1140 |
| gtggtgacag gaactatgaa agtgtaaaac aataattagt cttttcctga cgatttcaaa | 1200 |
| taaaatcttt gccactaaaa aaaaaaaaaa aaaaaa | 1236 |

<210> SEQ ID NO 16
<211> LENGTH: 342
<212> TYPE: PRT
<213> ORGANISM: Necator americanus

<400> SEQUENCE: 16

Met Ile Thr Ile Ile Thr Leu Leu Leu Ile Ala Ser Thr Val Lys Ser
1               5                   10                  15

Leu Thr Val Glu Glu Tyr Leu Ala Arg Pro Val Pro Glu Tyr Ala Thr
            20                  25                  30

Lys Leu Thr Gly Gln Ala Tyr Val Asp Tyr Val Asn Gln His Gln Ser
        35                  40                  45

Phe Tyr Lys Ala Glu Tyr Ser Pro Leu Val Glu Gln Tyr Ala Lys Ala
    50                  55                  60

Val Met Arg Ser Glu Phe Met Thr Lys Pro Asn Gln Asn Tyr Val Val
65                  70                  75                  80

Lys Asp Val Asp Leu Asn Ile Asn Leu Pro Glu Thr Phe Asp Ala Arg
                85                  90                  95

Glu Lys Trp Pro Asn Cys Thr Ser Ile Arg Thr Ile Arg Asp Gln Ser
            100                 105                 110

Asn Cys Gly Ser Cys Trp Ala Val Ser Ala Ala Ser Val Met Ser Asp
        115                 120                 125

Arg Leu Cys Ile Gln Ser Asn Gly Thr Ile Gln Ser Trp Ala Ser Asp
    130                 135                 140

Thr Asp Ile Leu Ser Cys Cys Trp Asn Cys Met Gly Cys Asp Gly
145                 150                 155                 160

Gly Arg Pro Phe Ala Ala Phe Phe Ala Ile Asp Asn Gly Val Cys
                165                 170                 175

Thr Gly Gly Pro Phe Arg Glu Pro Asn Val Cys Lys Pro Tyr Ala Phe 180                 185                 190
Tyr Pro Cys Gly Arg His Gln Asn Gln Lys Tyr Phe Gly Pro Cys Pro
                195                 200                 205
Lys Glu Leu Trp Pro Thr Pro Lys Cys Arg Lys Met Cys Gln Leu Lys
            210                 215                 220
Tyr Asn Val Ala Tyr Lys Asp Asp Lys Ile Tyr Gly Asn Asp Ala Tyr
225                 230                 235                 240
Ser Leu Pro Asn Asn Glu Thr Arg Ile Met Gln Glu Ile Phe Thr Asn
                245                 250                 255
Gly Pro Val Val Gly Ser Phe Ser Val Phe Ala Asp Phe Ala Ile Tyr
            260                 265                 270
Lys Lys Gly Val Tyr Val Ser Asn Gly Ile Gln Gln Asn Gly Ala His
            275                 280                 285
Ala Val Lys Ile Ile Gly Trp Gly Val Gln Asp Gly Leu Lys Tyr Trp
            290                 295                 300
Leu Ile Ala Asn Ser Trp Asn Asn Asp Trp Gly Asp Glu Gly Tyr Val
305                 310                 315                 320
Arg Phe Leu Arg Gly Asp Asn His Cys Gly Ile Glu Ser Arg Val Val
                325                 330                 335
Thr Gly Thr Met Lys Val
            340

<210> SEQ ID NO 17
<211> LENGTH: 789
<212> TYPE: DNA
<213> ORGANISM: Necator americanus

<400> SEQUENCE: 17
aagtgatggt tcattacaag ttaacctact tcgctatacg tggagccgga gaatgtgcaa     60
gacagatctt cgcacttgcc gatcaggaat tcgaggatgt ccgtttagac aaagagcagt    120
tcgcaaaagt gaagcctgat ttgcctttcg acaggttcc agtccttgaa gtcgatggca    180
agcaactggc tcaatccctt gcgatttgcc gctatctggc caggcagttc ggtttcgcag    240
gcaaatcaac gttcgatgaa gccgtagtcg actctttagc agaccagtat tctgactatc    300
gcgtcgagat caagtcgttc ttctacactg tcattggaat gcgagaaggt gatgtggagc    360
aactcaaaaa agaagtgtta cttcctgctc gcgataaatt cttcggattc atcactaaat    420
tccttaagaa aagcccttct ggtttccttg tcggtgactc actgacgtgg gtggacctct    480
tggtctcgga gcacaatgct acaatgctta cgtttgtacc agagttcctt gaaggctatc    540
ctgaagtaaa agagcacatg gaaaagatac gagcgattcc gaaactgaag aaatggatcg    600
aaacccgacc agagacattg ttctaattg tagtgatgtt atcctacttg ttctgatcta    660
tttgagttat cttcattgtc aacagaaatt cattattggc ttgcagtaat aaccgttatt    720
caggcacttg aaatccacta gttatttctt tccataagct acattctcag atgtatgtat    780
gaggataaa                                                            789

<210> SEQ ID NO 18
<211> LENGTH: 206
<212> TYPE: PRT
<213> ORGANISM: Necator americanus

<400> SEQUENCE: 18

Met Val His Tyr Lys Leu Thr Tyr Phe Ala Ile Arg Gly Ala Gly Glu
1               5                   10                  15

Cys Ala Arg Gln Ile Phe Ala Leu Ala Asp Gln Glu Phe Glu Asp Val

```
                  20                  25                  30
Arg Leu Asp Lys Glu Gln Phe Ala Lys Val Lys Pro Asp Leu Pro Phe
            35                  40                  45

Gly Gln Val Pro Val Leu Glu Val Asp Gly Lys Gln Leu Ala Gln Ser
        50                  55                  60

Leu Ala Ile Cys Arg Tyr Leu Ala Arg Gln Phe Gly Phe Ala Gly Lys
65                  70                  75                  80

Ser Thr Phe Asp Glu Ala Val Val Asp Ser Leu Ala Asp Gln Tyr Ser
                85                  90                  95

Asp Tyr Arg Val Glu Ile Lys Ser Phe Phe Tyr Thr Val Ile Gly Met
            100                 105                 110

Arg Glu Gly Asp Val Glu Gln Leu Lys Lys Glu Val Leu Leu Pro Ala
        115                 120                 125

Arg Asp Lys Phe Phe Gly Phe Ile Thr Lys Phe Leu Lys Lys Ser Pro
    130                 135                 140

Ser Gly Phe Leu Val Gly Asp Ser Leu Thr Trp Val Asp Leu Leu Val
145                 150                 155                 160

Ser Glu His Asn Ala Thr Met Leu Thr Phe Val Pro Glu Phe Leu Glu
                165                 170                 175

Gly Tyr Pro Glu Val Lys Glu His Met Glu Lys Ile Arg Ala Ile Pro
            180                 185                 190

Lys Leu Lys Lys Trp Ile Glu Thr Arg Pro Glu Thr Leu Phe
        195                 200                 205

<210> SEQ ID NO 19
<211> LENGTH: 722
<212> TYPE: DNA
<213> ORGANISM: Schistosoma mansoni

<400> SEQUENCE: 19
aaatggctct tggttgtggg tataagtgtt tgcagtgttt gctaattatt ttcaactgtg      60
gagcattcat atgtggtctc gggctgattg tggttggtgc acttgggctc cattctgttg     120
taaatcactg gagcgaaatt gaaccccac tacaatctct tattatcttc attattgctc      180
tcggatgctt cttatttgtt ttgggggctt tagggatgtt tggagcatgc atgaagaatg     240
tttgtttatt aacgacgtat tgcattcttc tatcaatttt aatggttgcc gaaatagcag     300
caggaatatt tgctatagta gaaaagccca aggtcaaaaa acacatcact agtgcattaa     360
aaaaattagt agataagtac cgtaatgacg aacatgttcg aaaagttttt gatgaaatcc     420
aacaaaaatt acattgctgt ggtgctgact ctcctaaaga ttatggcgaa atccaccga      480
catcatgttc aaaagatggc gtacaattta cagagggatg tattaaaaag gtcagcgatc     540
taagcaaagc gcacctcaat gctatcatag ttagcgtgtt tctgttcgca ttggtccaaa     600
tgatttgtct agtatttgca gtatgtgttc tattggctat aaagcgcggt gacgatgaat     660
acaatgacat tacgaaaacg cttagtgaaa aataaaccg aaaacaacca ttaaaaaatt     720
aa                                                                   722

<210> SEQ ID NO 20
<211> LENGTH: 239
<212> TYPE: PRT
<213> ORGANISM: Schistosoma mansoni

<400> SEQUENCE: 20

Met Ala Leu Gly Cys Gly Tyr Lys Cys Leu Gln Cys Leu Leu Ile Ile
1               5                   10                  15
```

```
Phe Asn Cys Gly Ala Phe Ile Cys Gly Leu Gly Leu Ile Val Val Gly
            20                  25                  30

Ala Leu Gly Leu His Ser Val Val Asn His Trp Ser Glu Ile Glu Pro
        35                  40                  45

Pro Leu Gln Ser Leu Ile Ile Phe Ile Ile Ala Leu Gly Cys Phe Leu
50                  55                  60

Phe Val Leu Gly Ala Leu Gly Met Phe Gly Ala Cys Met Lys Asn Val
65                  70                  75                  80

Cys Leu Leu Thr Thr Tyr Cys Ile Leu Leu Ser Ile Leu Met Val Ala
                85                  90                  95

Glu Ile Ala Ala Gly Ile Phe Ala Ile Val Lys Pro Lys Val Lys
            100                 105                 110

Lys His Ile Thr Ser Ala Leu Lys Lys Leu Val Asp Lys Tyr Arg Asn
        115                 120                 125

Asp Glu His Val Arg Lys Val Phe Asp Glu Ile Gln Gln Lys Leu His
130                 135                 140

Cys Cys Gly Ala Asp Ser Pro Lys Asp Tyr Gly Glu Asn Pro Pro Thr
145                 150                 155                 160

Ser Cys Ser Lys Asp Gly Val Gln Phe Thr Glu Gly Cys Ile Lys Lys
                165                 170                 175

Val Ser Asp Leu Ser Lys Ala His Leu Asn Ala Ile Ile Val Ser Val
            180                 185                 190

Phe Leu Phe Ala Leu Val Gln Met Ile Cys Leu Val Phe Ala Val Cys
        195                 200                 205

Val Leu Leu Ala Ile Lys Arg Gly Asp Asp Glu Tyr Asn Asp Ile Thr
210                 215                 220

Lys Thr Leu Ser Glu Lys Ile Asn Arg Lys Gln Pro Leu Lys Asn
225                 230                 235
```

<210> SEQ ID NO 21
<211> LENGTH: 576
<212> TYPE: DNA
<213> ORGANISM: Schistosoma mansoni

<400> SEQUENCE: 21

| | |
|---|---|
| atgaaaagtg gctgggagta tattggaatc tttttgtaca ttatggtgaa tattctggat | 60 |
| aaacaacgat gtcattcagt gcgttgctac gtctgtgatt attgtccgat agtaacaagc | 120 |
| gtatcaatat cagaagagaa caactgtaca tcttgctcaa cggctggtta taattattcg | 180 |
| attcacagaa tatgcgtgtt taaggatggc atacccatta acttcccaaa cgaaaatcga | 240 |
| acgcagtgta acactgattt gtgtaacggg ttaacagttg ataacactgg aaaaattcca | 300 |
| tcagttccta tagcaaatcc atttcgttgc tatacgtgtt tgaattgtac aaaaagtaac | 360 |
| caaaaggtac ttagcggttg tggtgcatgt gtgacaactc gtggttctgg aattatcagt | 420 |
| aaattttgtg gaactacatg tgaaagattg tatattgacg atcaaattag ttgttgctca | 480 |
| acagatctat gtaacggaat gacaaaatta tctattcatc gtcatgttat tattgttctg | 540 |
| tttgtttgca taggaatcag taaatacatt ctatga | 576 |

<210> SEQ ID NO 22
<211> LENGTH: 191
<212> TYPE: PRT
<213> ORGANISM: Schistosoma mansoni

<400> SEQUENCE: 22

```
Met Lys Ser Gly Trp Glu Tyr Ile Gly Ile Phe Leu Tyr Ile Met Val
1               5                   10                  15
```

```
Asn Ile Leu Asp Lys Gln Arg Cys His Ser Val Arg Cys Tyr Val Cys
                20                  25                  30

Asp Tyr Cys Pro Ile Val Thr Ser Val Ser Ile Ser Glu Glu Asn Asn
            35                  40                  45

Cys Thr Ser Cys Ser Thr Ala Gly Tyr Asn Tyr Ser Ile His Arg Ile
 50                  55                  60

Cys Val Phe Lys Asp Gly Ile Pro Ile Asn Phe Pro Asn Glu Asn Arg
 65                  70                  75                  80

Thr Gln Cys Asn Thr Asp Leu Cys Asn Gly Leu Thr Val Asp Asn Thr
                85                  90                  95

Gly Lys Ile Pro Ser Val Pro Ile Ala Asn Pro Phe Arg Cys Tyr Thr
            100                 105                 110

Cys Leu Asn Cys Thr Lys Ser Asn Gln Lys Val Leu Ser Gly Cys Gly
        115                 120                 125

Ala Cys Val Thr Thr Arg Gly Ser Gly Ile Ile Ser Lys Phe Cys Gly
    130                 135                 140

Thr Thr Cys Glu Arg Leu Tyr Ile Asp Asp Gln Ile Ser Cys Cys Ser
145                 150                 155                 160

Thr Asp Leu Cys Asn Gly Met Thr Lys Leu Ser Ile His Arg His Val
                165                 170                 175

Ile Ile Val Leu Phe Val Cys Ile Gly Ile Ser Lys Tyr Ile Leu
            180                 185                 190

<210> SEQ ID NO 23
<211> LENGTH: 660
<212> TYPE: DNA
<213> ORGANISM: Schistosoma haematobium

<400> SEQUENCE: 23
atggctcttg gttgtgggta taagtgttcg caatgtttgc tagttatttt caattgtgga      60
gcgttcatat gtggtctcgg gctgattgtg gttggtgcac ttgggctcca ttctgttgta     120
aatcactgga agacattga acctccatta caatcgctta ttatctttat tattgtcctc     180
ggatgcttct tatttgtttt gggggcctta ggaatgtttg cgcctgcac gaagaatgtg      240 tgtttattaa caacgtattg tattcttta tcaattttga tagttgccga aatagcagca     300
ggaatatttg caatattgga aaagccaaag gtaaaaaaac acgtcactga tgcattaaga    360
gaattcgtaa aagagtactc tcacgacgaa catgttagca agttcttga tgaagttcaa     420 cagaaattac aatgctgtgg tgctgattct tcaaaagatt atgtcactcc accaccggaa    480
tcctgtttca agatggcca aatatttaaa gagggatgcg ttaaaaaggt cagtgatcta    540
agcaaaatgc acctcaatgc tatcataatt agcgtatttc tgttctcatt ggtccaaatg   600
atttgtctgg tatttgcagt atgtgttcta ttggctgtaa agcgcggtga tgatgaatag   660

<210> SEQ ID NO 24
<211> LENGTH: 219
<212> TYPE: PRT
<213> ORGANISM: Schistosoma haematobium

<400> SEQUENCE: 24

Met Ala Leu Gly Cys Gly Tyr Lys Cys Ser Gln Cys Leu Leu Val Ile
 1               5                  10                  15

Phe Asn Cys Gly Ala Phe Ile Cys Gly Leu Gly Leu Ile Val Val Gly
                20                  25                  30

Ala Leu Gly Leu His Ser Val Val Asn His Trp Lys Asp Ile Glu Pro
            35                  40                  45
```

Pro Leu Gln Ser Leu Ile Ile Phe Ile Ile Val Leu Gly Cys Phe Leu
           50                  55                  60

Phe Val Leu Gly Ala Leu Gly Met Phe Gly Ala Cys Thr Lys Asn Val
 65                  70                  75                  80

Cys Leu Leu Thr Thr Tyr Cys Ile Leu Leu Ser Ile Leu Ile Val Ala
                 85                  90                  95

Glu Ile Ala Ala Gly Ile Phe Ala Ile Leu Glu Lys Pro Lys Val Lys
                100                 105                 110

Lys His Val Thr Asp Ala Leu Arg Glu Phe Val Lys Glu Tyr Ser His
            115                 120                 125

Asp Glu His Val Ser Lys Val Leu Asp Glu Val Gln Gln Lys Leu Gln
130                 135                 140

Cys Cys Gly Ala Asp Ser Ser Lys Asp Tyr Val Thr Pro Pro Glu
145                 150                 155                 160

Ser Cys Phe Lys Asp Gly Gln Ile Phe Lys Glu Gly Cys Val Lys Lys
                165                 170                 175

Val Ser Asp Leu Ser Lys Met His Leu Asn Ala Ile Ile Ser Val
            180                 185                 190

Phe Leu Phe Ser Leu Val Gln Met Ile Cys Leu Val Phe Ala Val Cys
                195                 200                 205

Val Leu Leu Ala Val Lys Arg Gly Asp Asp Glu
            210                 215

<210> SEQ ID NO 25
<211> LENGTH: 672
<212> TYPE: DNA
<213> ORGANISM: Schistosoma mansoni

<400> SEQUENCE: 25
atgtttctat cacaattaca aaagtattgg aataatatat ttattatatc caatctacta      60
ttcattgtat tcgatatagc tttattggca ttacctatta gaacattaga tgtcttagct     120
aattacaata caattttaga ttattttaaa ccagtgatct ttccagttgt catctttaca     180
gggattcttg actattgag tgttttata ggtttcattg gattatggaa aagaagact       240
gttttcattt tggtgcacat tgtcgggttg actattgcaa caattattga aatctctata     300
tctataagat caagtttacg gaaaaatcag ttcttcaaag tagctaatca atcattatgg     360
aattctattc aatattatga aaaacatcca aattatgaaa tcaagtgga taatctacaa     420
agagagtttt tttgttgtgg tgttagatca tatacagatt ataaaagacc ggtaattacc     480
ctaccacttt cttgtaaaac aggcaattca attcatccaa aaggttgtgc tgaagcccta     540
tatgattata tacaacattg tatcatgata ataatatata tatgcattgc attcgctatc     600
attaaagcta tctatttggc cacttctatt cttctatatc gtaaatctga agaataat      660
ttatctgtat aa                                                         672

<210> SEQ ID NO 26
<211> LENGTH: 223
<212> TYPE: PRT
<213> ORGANISM: Schistosoma mansoni

<400> SEQUENCE: 26

Met Phe Leu Ser Gln Leu Gln Lys Tyr Trp Asn Asn Ile Phe Ile Ile
 1               5                  10                  15

Ser Asn Leu Leu Phe Ile Val Phe Asp Ile Ala Leu Leu Ala Leu Pro
             20                  25                  30

```
Ile Arg Thr Leu Asp Val Leu Ala Asn Tyr Asn Thr Ile Leu Asp Tyr
            35                  40                  45

Phe Lys Pro Val Ile Phe Pro Val Val Ile Phe Thr Gly Ile Leu Gly
    50                  55                  60

Leu Leu Ser Val Phe Ile Gly Phe Ile Gly Leu Trp Lys Lys Thr
65                  70                  75                  80

Val Phe Ile Leu Val His Ile Val Gly Leu Thr Ile Ala Thr Ile Ile
                85                  90                  95

Glu Ile Ser Ile Ser Ile Arg Ser Ser Leu Arg Lys Asn Gln Phe Phe
                100                 105                 110

Lys Val Ala Asn Gln Ser Leu Trp Asn Ser Ile Gln Tyr Tyr Glu Lys
            115                 120                 125

His Pro Asn Tyr Glu Asn Gln Val Asp Asn Leu Gln Arg Glu Phe Phe
        130                 135                 140

Cys Cys Gly Val Arg Ser Tyr Thr Asp Tyr Lys Arg Pro Val Ile Thr
145                 150                 155                 160

Leu Pro Leu Ser Cys Lys Thr Gly Asn Ser Ile His Pro Lys Gly Cys
                165                 170                 175

Ala Glu Ala Leu Tyr Asp Tyr Ile Gln His Cys Ile Met Ile Ile Ile
            180                 185                 190

Tyr Ile Cys Ile Ala Phe Ala Ile Ile Lys Ala Ile Tyr Leu Ala Thr
        195                 200                 205

Ser Ile Leu Leu Tyr Arg Lys Ser Glu Lys Asn Asn Leu Ser Val
    210                 215                 220
```

<210> SEQ ID NO 27
<211> LENGTH: 846
<212> TYPE: DNA
<213> ORGANISM: Schistosoma mansoni

<400> SEQUENCE: 27

```
atgttgtgca acctaccatg tcgaattgtt ttgattgtta tgaacactgt cagcatgatt      60
gtagggctgg tactgctcat acttggagcc ttgatggttt ggggtcaaag tgttattcaa     120
tccttgttga ataatttcat aaccaaccta attaatcagt acattaaagg aactgatagt     180
ggacaaatta tgaaatggt cacacgaata ctgacgtcta cttctccagt tggtatggca     240
gtttttatac taggtgctgt ttgtacaggt atctcgttgt ttggttattg tggagcctgt     300
tgtaatatga agatattact ttatatatac gcaatttag taggagcatt ggcacttgct     360
ttcctgatca cattcagtgt gtacttctct cgtaaagatg agattggaaa cagagcaatt     420
gacctattcg agacaagtgt caagaattat caatcaatgg cagcaaatac aattgacagc     480
ttagtggttg gcttaatctc acctccactt caatgttgtg gtgtgaataa tggagatgac     540
tttacaactt cacctaattt ctggagaaat gacacttacg gtggtaaaac atataataat     600
attgcatatc ctgtagtatg ttgcaaattg aatcaaaatt atgcaattat tgattctaca     660
tgtccagatc aatttaatga aaataacagt aattataaaa ctggttgtag aggtccatta     720
aaagaacttt tccttaaata tatggacttt gtagcttatg gattaattgc ggcatttgtt     780
atattggtaa gtattattgc ttttataaaa atttatttcg agttactttt tttcgtcttt     840
aattaa                                                                846
```

<210> SEQ ID NO 28
<211> LENGTH: 281
<212> TYPE: PRT
<213> ORGANISM: Schistosoma mansoni -continued

<400> SEQUENCE: 28

```
Met Leu Cys Asn Leu Pro Cys Arg Ile Val Leu Ile Val Met Asn Thr
1               5                   10                  15

Val Ser Met Ile Val Gly Leu Val Leu Leu Ile Leu Gly Ala Leu Met
            20                  25                  30

Val Trp Gly Gln Ser Val Ile Gln Ser Leu Leu Asn Asn Phe Ile Thr
        35                  40                  45

Asn Leu Ile Asn Gln Tyr Ile Lys Gly Thr Asp Ser Gly Gln Ile Asn
    50                  55                  60

Glu Met Val Thr Arg Ile Leu Thr Ser Thr Ser Pro Val Gly Met Ala
65                  70                  75                  80

Val Phe Ile Leu Gly Ala Val Cys Thr Gly Ile Ser Leu Phe Gly Tyr
                85                  90                  95

Cys Gly Ala Cys Cys Asn Met Lys Ile Leu Leu Tyr Ile Tyr Ala Ile
            100                 105                 110

Leu Val Gly Ala Leu Ala Leu Ala Phe Leu Ile Thr Phe Ser Val Tyr
        115                 120                 125

Phe Ser Arg Lys Asp Glu Ile Gly Asn Arg Ala Ile Asp Leu Phe Glu
    130                 135                 140

Thr Ser Val Lys Asn Tyr Gln Ser Met Ala Ala Asn Thr Ile Asp Ser
145                 150                 155                 160

Leu Val Val Gly Leu Ile Ser Pro Pro Leu Gln Cys Cys Gly Val Asn
                165                 170                 175

Asn Gly Asp Asp Phe Thr Thr Ser Pro Asn Phe Trp Arg Asn Asp Thr
            180                 185                 190

Tyr Gly Gly Lys Thr Tyr Asn Asn Ile Ala Tyr Pro Val Val Cys Cys
        195                 200                 205

Lys Leu Asn Gln Asn Tyr Ala Ile Ile Asp Ser Thr Cys Pro Asp Gln
    210                 215                 220

Phe Asn Glu Asn Asn Ser Asn Tyr Lys Thr Gly Cys Arg Gly Pro Leu
225                 230                 235                 240

Lys Glu Leu Phe Leu Lys Tyr Met Asp Phe Val Ala Tyr Gly Leu Ile
                245                 250                 255

Ala Ala Phe Val Ile Leu Val Ser Ile Ile Ala Phe Ile Lys Ile Tyr
            260                 265                 270

Phe Glu Leu Leu Phe Phe Val Phe Asn
        275                 280

<210> SEQ ID NO 29
<211> LENGTH: 1366
<212> TYPE: DNA
<213> ORGANISM: Necator americanus

<400> SEQUENCE: 29
ggcacgagag aatgcgttcg atactcgtgt tggtggctct gatcggatgc attgctgcgg      60
gtgtatataa aatcccattg aaaagaatca ctccgccgat gataaaaatg ttgagagctg     120
gtacttggga aacgtacgta gaaggaatga ggaagagaca attacagtta ctgaaggagc     180
acaaggttca tatccaagat gtactcggct atgctaacat ggagtacctc ggcgaaatta     240
ctattggaac tcctcaacag aagtttctgg tggttttgga cactggctcc tcgaatctgt     300
gggtccctga tgattcatgc tacaaggaga gagacctga tagatgtcta gtatcaaact      360
gtgatgctgg actggtttgt caagtcttct gtccagatcc taaatgctgt gaacatacga     420
gagaattcaa gcaagtaaac gcatgcaaag ataagcatcg atttgatcaa aagaattcca     480
```

-continued

```
acacttatgt taaaacaaac aaaacatggg caatagcgta tggaactgga gatgcgaggg    540
gatttttgg aagagataca gtccgtttgg gtgctgaagg aaaggatcag ctcgttatta    600
atgatacgtg gttcggacaa gcagagcata tagctgaatt tttcagtaat actttccttg    660
atggcattct cggactcgct tttcaagaac tgtcagaagg aggcgtcgct cctccaataa    720
ttcgtgccat tgaccttgga cttctcgatc aaccaatatt tactgtctat ttcgaaaatg    780
tcggagacaa agaaggtgtt tatggaggtg ttttcacctg gggtggtctc gatcccgatc    840
attgcgaaga tgaggtcaca tatgaacagc taaccgaagc aacttactgg cagtttagac    900
ttaaaggagt gtcgtctaag aacttctcgt cgacggctgg ttgggaagca atatccgaca    960
ctggtacctc gttaaatgga gcccctaggg ggatactaag aagtattgca agacagtata   1020
atggacagta cgtcgcatct caaggtctct acgtcgtcga ctgcagtaaa aatgtgaccg   1080
ttgacgtgac cattggcgac agaaactaca ctatgactgc gaaaaatctc gtacttgaaa   1140
tacaggctga tatatgtatt atggcatttt tcgaaatgga catgttcatt ggaccagcat   1200
ggattcttgg cgatccattt attcgagaat attgcaatat tcatgacatt gaaaagaagc   1260
ggattggttt tgcagctgta aaacattgat cgattataaa tgtaatgggc tatttgtcat   1320
aaattgctca ataaagtttt ttgactaaaa aaaaaaaaaa aaaaaa                   1366
```

<210> SEQ ID NO 30
<211> LENGTH: 425
<212> TYPE: PRT
<213> ORGANISM: Necator americanus

<400> SEQUENCE: 30

```
Met Arg Ser Ile Leu Val Leu Val Ala Leu Ile Gly Cys Ile Ala Ala
1               5                   10                  15

Gly Val Tyr Lys Ile Pro Leu Lys Arg Ile Thr Pro Pro Met Ile Lys
            20                  25                  30

Met Leu Arg Ala Gly Thr Trp Glu Thr Tyr Val Glu Gly Met Arg Lys
        35                  40                  45

Arg Gln Leu Gln Leu Leu Lys Glu His Lys Val His Ile Gln Asp Val
    50                  55                  60

Leu Gly Tyr Ala Asn Met Glu Tyr Leu Gly Glu Ile Thr Ile Gly Thr
65                  70                  75                  80

Pro Gln Gln Lys Phe Leu Val Val Leu Asp Thr Gly Ser Ser Asn Leu
                85                  90                  95

Trp Val Pro Asp Asp Ser Cys Tyr Lys Glu Lys Arg Pro Asp Arg Cys
            100                 105                 110

Leu Val Ser Asn Cys Asp Ala Gly Leu Val Cys Gln Val Phe Cys Pro
        115                 120                 125

Asp Pro Lys Cys Cys Glu His Thr Arg Glu Phe Lys Gln Val Asn Ala
    130                 135                 140

Cys Lys Asp Lys His Arg Phe Asp Gln Lys Asn Ser Asn Thr Tyr Val
145                 150                 155                 160

Lys Thr Asn Lys Thr Trp Ala Ile Ala Tyr Gly Thr Gly Asp Ala Arg
                165                 170                 175

Gly Phe Phe Gly Arg Asp Thr Val Arg Leu Gly Ala Glu Gly Lys Asp
            180                 185                 190

Gln Leu Val Ile Asn Asp Thr Trp Phe Gly Gln Ala Glu His Ile Ala
        195                 200                 205

Glu Phe Ser Asn Thr Phe Leu Asp Gly Ile Leu Gly Leu Ala Phe
    210                 215                 220
```

```
Gln Glu Leu Ser Glu Gly Gly Val Ala Pro Pro Ile Ile Arg Ala Ile
225                 230                 235                 240

Asp Leu Gly Leu Leu Asp Gln Pro Ile Phe Thr Val Tyr Phe Glu Asn
            245                 250                 255

Val Gly Asp Lys Glu Gly Val Tyr Gly Gly Val Phe Thr Trp Gly Gly
        260                 265                 270

Leu Asp Pro Asp His Cys Glu Asp Glu Val Thr Tyr Glu Gln Leu Thr
    275                 280                 285

Glu Ala Thr Tyr Trp Gln Phe Arg Leu Lys Gly Val Ser Ser Lys Asn
290                 295                 300

Phe Ser Ser Thr Ala Gly Trp Glu Ala Ile Ser Asp Thr Gly Thr Ser
305                 310                 315                 320

Leu Asn Gly Ala Pro Arg Gly Ile Leu Arg Ser Ile Ala Arg Gln Tyr
            325                 330                 335

Asn Gly Gln Tyr Val Ala Ser Gln Gly Leu Tyr Val Val Asp Cys Ser
        340                 345                 350

Lys Asn Val Thr Val Asp Val Thr Ile Gly Asp Arg Asn Tyr Thr Met
    355                 360                 365

Thr Ala Lys Asn Leu Val Leu Glu Ile Gln Ala Asp Ile Cys Ile Met
370                 375                 380

Ala Phe Phe Glu Met Asp Met Phe Ile Gly Pro Ala Trp Ile Leu Gly
385                 390                 395                 400

Asp Pro Phe Ile Arg Glu Tyr Cys Asn Ile His Asp Ile Glu Lys Lys
            405                 410                 415

Arg Ile Gly Phe Ala Ala Val Lys His
        420                 425

<210> SEQ ID NO 31
<211> LENGTH: 831
<212> TYPE: DNA
<213> ORGANISM: Artificial Sequence
<220> FEATURE:
<223> OTHER INFORMATION: Nucleic acid sequence encoding a synthetic
      chimeric protein

<400> SEQUENCE: 31
atggttcatt acaagttaac ctacttcgct atacgtggag ccggagaatg tgcaagacag      60
atcttcgcac ttgccgatca ggaattcgag gatgtccgtt tagacaaaga gcagttcgca     120
aaagtgaagc tgatttgcc tttcggacag gttccagtcc ttgaagtcga tggcaagcaa     180
ctggctcaat cccttgcgat tgccgctat ctggccaggc agttcggttt cgcaggcaaa     240
tcaacgttcg atgaagccgt agtcgactct ttagcagacc agtattctga ctatcgcgtc     300
gagatcaagt cgttcttcta cactgtcatt ggaatgcgag aaggtgatgt ggagcaactc     360
aaaaaagaag tgttacttcc tgctcgcgat aaattcttcg gattcatcac taaattcctt     420
aagaaaagcc cttctggttt ccttgtcggt gactcactga cgtgggtgga cctcttggtc     480
tcggagcaca atgctacaat gcttacgttt gtaccagagt tccttgaagg ctatcctgaa     540
gtaaaagagc acatggaaaa gatacgagcg attccgaaac tgaagaaatg gatcgaaacc     600
cgaccagaga cattgttcgg taccggtggt ggctccggtg atgacgacga caagagtccc     660
atgggtaggg cggcaagcag cagcattgcg tgcccgaacg gctgtcaggc gattgcggat     720
accggcacca gcctgattgc gggtccgaaa gcgcaggtgg aagcgattca gaaatatatt     780
ggcgcggaac cgctgatgct cgagcaccac caccaccacc accactaa                 831

<210> SEQ ID NO 32
```

<211> LENGTH: 276
<212> TYPE: PRT
<213> ORGANISM: Artificial Sequence
<220> FEATURE:
<223> OTHER INFORMATION: Synthetic chimeric protein

<400> SEQUENCE: 32

```
Met Val His Tyr Lys Leu Thr Tyr Phe Ala Ile Arg Gly Ala Gly Glu
1               5                   10                  15
Cys Ala Arg Gln Ile Phe Ala Leu Ala Asp Gln Glu Phe Glu Asp Val
            20                  25                  30
Arg Leu Asp Lys Glu Gln Phe Ala Lys Val Lys Pro Asp Leu Pro Phe
        35                  40                  45
Gly Gln Val Pro Val Leu Glu Val Asp Gly Lys Gln Leu Ala Gln Ser
    50                  55                  60
Leu Ala Ile Cys Arg Tyr Leu Ala Arg Gln Phe Gly Phe Ala Gly Lys
65                  70                  75                  80
Ser Thr Phe Asp Glu Ala Val Val Asp Ser Leu Ala Asp Gln Tyr Ser
                85                  90                  95
Asp Tyr Arg Val Glu Ile Lys Ser Phe Phe Tyr Thr Val Ile Gly Met
            100                 105                 110
Arg Glu Gly Asp Val Glu Gln Leu Lys Lys Glu Val Leu Leu Pro Ala
        115                 120                 125
Arg Asp Lys Phe Phe Gly Phe Ile Thr Lys Phe Leu Lys Lys Ser Pro
    130                 135                 140
Ser Gly Phe Leu Val Gly Asp Ser Leu Thr Trp Val Asp Leu Leu Val
145                 150                 155                 160
Ser Glu His Asn Ala Thr Met Leu Thr Phe Val Pro Glu Phe Leu Glu
                165                 170                 175
Gly Tyr Pro Glu Val Lys Glu His Met Glu Lys Ile Arg Ala Ile Pro
            180                 185                 190
Lys Leu Lys Lys Trp Ile Glu Thr Arg Pro Gly Thr Leu Phe Gly Thr
        195                 200                 205
Gly Gly Gly Ser Gly Asp Asp Asp Asp Lys Ser Pro Met Gly Arg Ala
    210                 215                 220
Ala Ser Ser Ser Ile Ala Cys Pro Asn Gly Cys Gln Ala Ile Ala Asp
225                 230                 235                 240
Thr Gly Thr Ser Leu Ile Ala Gly Pro Lys Ala Gln Val Glu Ala Ile
                245                 250                 255
Gln Lys Tyr Ile Gly Ala Glu Pro Leu Met Leu Glu His His His His
            260                 265                 270
His His His His
        275
```

<210> SEQ ID NO 33
<211> LENGTH: 450
<212> TYPE: DNA
<213> ORGANISM: Artificial Sequence
<220> FEATURE:
<223> OTHER INFORMATION: Nucleic acid sequence encoding a synthetic chimeric protein

<400> SEQUENCE: 33

```
atggaaaagc ccaaggtcaa aaacacatca actagtgcat taaaaaaatt agtagataag      60
taccgtaatg acgaacatgt tcgaaaagtt tttgatgaaa tccaacaaaa attacattgc     120
tgtggtgctg actctcctaa agattatggc gaaatccac cgacatcatg ttcaaaagat     180
ggcgtacaat ttacagaggg atgtattaaa aaggtcagcg atctaagcaa agcgcacggt     240
```

```
accggtggtg gctccggtga tgacgacgac aagagtccca tgggtagggc ggcaagcagc    300
agcattgcgt gcccgaacgg ctgtcaggcg attgcggata ccggcaccag cctgattgcg    360
ggtccgaaag cgcaggtgga agcgattcag aaatatattg gcgcggaacc gctgatgctc    420
gagcaccacc accaccacca ccaccactaa                                     450
```

<210> SEQ ID NO 34
<211> LENGTH: 149
<212> TYPE: PRT
<213> ORGANISM: Artificial Sequence
<220> FEATURE:
<223> OTHER INFORMATION: Synthetic chimeric protein

<400> SEQUENCE: 34

```
Met Glu Lys Pro Lys Val Lys Lys His Ile Thr Ser Ala Leu Lys Lys
1               5                   10                  15

Leu Val Asp Lys Tyr Arg Asn Asp Glu His Val Arg Lys Val Phe Asp
            20                  25                  30

Glu Ile Gln Gln Lys Leu His Cys Cys Gly Ala Asp Ser Pro Lys Asp
        35                  40                  45

Tyr Gly Glu Asn Pro Pro Thr Ser Cys Ser Lys Asp Gly Val Gln Phe
    50                  55                  60

Thr Glu Gly Cys Ile Lys Lys Val Ser Asp Leu Ser Lys Ala His Gly
65                  70                  75                  80

Thr Gly Gly Gly Ser Gly Asp Asp Asp Lys Ser Pro Met Gly Arg
                85                  90                  95

Ala Ala Ser Ser Ser Ile Ala Cys Pro Asn Gly Cys Gln Ala Ile Ala
                100                 105                 110

Asp Thr Gly Thr Ser Leu Ile Ala Gly Pro Lys Ala Gln Val Glu Ala
            115                 120                 125

Ile Gln Lys Tyr Ile Gly Ala Glu Pro Leu Met Leu Glu His His His
        130                 135                 140

His His His His His
145
```

<210> SEQ ID NO 35
<211> LENGTH: 942
<212> TYPE: DNA
<213> ORGANISM: Artificial Sequence
<220> FEATURE:
<223> OTHER INFORMATION: Nucleic acid sequence encoding a synthetic
      chimeric protein

<400> SEQUENCE: 35

```
atggttcatt acaagttaac ctacttcgct atacgtggag ccggagaatg tgcaagacag    60
atcttcgcac ttgccgatca ggaattcgag gatgtccgtt tagacaaaga gcagttcgca   120
aaagtgaagc ctgatttgcc tttcggacag gttccagtcc ttgaagtcga tgcaagcaa    180 ctggctcaat cccttgcgat tgccgctat ctggccaggc agttcggttt cgcaggcaaa    240
tcaacgttcg atgaagccgt agtcgactct ttagcagacc agtattctga ctatcgcgtc    300
gagatcaagt cgttcttcta cactgtcatt ggaatgcgag aaggtgatgt ggagcaactc    360
aaaaaagaag tgttacttcc tgctcgcgat aaattcttcg gattcatcac taaattcctt    420
aagaaaagcc cttctggttt ccttgtcggt gactcactga cgtgggtgga cctcttggtc    480
tcggagcaca atgctacaat gcttacgttt gtaccagagt tccttgaagg ctatcctgaa    540
gtaaaagagc acatggaaaa gatacgagcg attccgaaac tgaagaaatg gatcgaaacc   600
```

```
cgaccagaga cattgttcgg taccggtggt ggctccggtg atgacgacga caagagtccc    660
atgggtaggg cggcagaaaa gcccaaggtc aaaaaacaca tcactagtgc attaaaaaaa    720
ttagtagata agtaccgtaa tgacgaacat gttcgaaaag ttttgatga atccaacaa      780 aaattacatt gctgtggtgc tgactctcct aaagattatg gcgaaaatcc accgacatca    840
tgttcaaaag atggcgtaca atttacagag ggatgtatta aaaggtcag cgatctaagc     900 aaagcgcacc tcgagcacca ccaccaccac caccaccact aa                      942
```

```
<210> SEQ ID NO 36
<211> LENGTH: 313
<212> TYPE: PRT
<213> ORGANISM: Artificial Sequence
<220> FEATURE:
<223> OTHER INFORMATION: Synthetic chimeric protein

<400> SEQUENCE: 36
```

```
Met Val His Tyr Lys Leu Thr Tyr Phe Ala Ile Arg Gly Ala Gly Glu
1               5                   10                  15

Cys Ala Arg Gln Ile Phe Ala Leu Ala Asp Gln Glu Phe Glu Asp Val
            20                  25                  30

Arg Leu Asp Lys Glu Gln Phe Ala Lys Val Lys Pro Asp Leu Pro Phe
        35                  40                  45

Gly Gln Val Pro Val Leu Glu Val Asp Gly Lys Gln Leu Ala Gln Ser
    50                  55                  60

Leu Ala Ile Cys Arg Tyr Leu Ala Arg Gln Phe Gly Phe Ala Gly Lys
65                  70                  75                  80

Ser Thr Phe Asp Glu Ala Val Val Asp Ser Leu Ala Asp Gln Tyr Ser
                85                  90                  95

Asp Tyr Arg Val Glu Ile Lys Ser Phe Phe Tyr Thr Val Ile Gly Met
            100                 105                 110

Arg Glu Gly Asp Val Glu Gln Leu Lys Lys Glu Val Leu Leu Pro Ala
        115                 120                 125

Arg Asp Lys Phe Phe Gly Phe Ile Thr Lys Phe Leu Lys Lys Ser Pro
    130                 135                 140

Ser Gly Phe Leu Val Gly Asp Ser Leu Thr Trp Val Asp Leu Leu Val
145                 150                 155                 160

Ser Glu His Asn Ala Thr Met Leu Thr Phe Val Pro Glu Phe Leu Glu
                165                 170                 175

Gly Tyr Pro Glu Val Lys Glu His Met Glu Lys Ile Arg Ala Ile Pro
            180                 185                 190

Lys Leu Lys Lys Trp Ile Glu Thr Arg Pro Glu Thr Leu Phe Gly Thr
        195                 200                 205

Gly Gly Gly Ser Gly Asp Asp Asp Lys Ser Pro Met Gly Arg Ala
    210                 215                 220

Ala Glu Lys Pro Lys Val Lys Lys His Ile Thr Ser Ala Leu Lys Lys
225                 230                 235                 240

Leu Val Asp Lys Tyr Arg Asn Asp Glu His Val Arg Lys Val Phe Asp
                245                 250                 255

Glu Ile Gln Gln Lys Leu His Cys Cys Gly Ala Asp Ser Pro Lys Asp
            260                 265                 270

Tyr Gly Glu Asn Pro Pro Thr Ser Cys Ser Lys Asp Gly Val Gln Phe
        275                 280                 285

Thr Glu Gly Cys Ile Lys Lys Val Ser Asp Leu Ser Lys Ala His Leu
    290                 295                 300

Glu His His His His His His His His
```

<210> SEQ ID NO 37
<211> LENGTH: 57
<212> TYPE: PRT
<213> ORGANISM: Artificial Sequence
<220> FEATURE:
<223> OTHER INFORMATION: Synthetic fragment 5 from Necator americanus

<400> SEQUENCE: 37

Val Thr Arg Arg Gly Tyr Trp Gln Phe Lys Met Asp Met Val Gln Gly
1               5                   10                  15

Gly Ser Ser Ile Ala Cys Pro Asn Gly Cys Gln Ala Ile Ala Asp Thr
            20                  25                  30

Gly Thr Ser Leu Ile Ala Gly Pro Lys Ala Gln Val Glu Ala Ile Gln
        35                  40                  45

Lys Tyr Ile Gly Ala Glu Pro Leu Met
    50                  55

<210> SEQ ID NO 38
<211> LENGTH: 57
<212> TYPE: PRT
<213> ORGANISM: Artificial Sequence
<220> FEATURE:
<223> OTHER INFORMATION: Synthetic peptide Fragment 5 homolog from
      Ancylostoma ceylanicum

<400> SEQUENCE: 38

Val Thr Arg Arg Gly Tyr Trp Gln Phe Lys Met Asp Lys Val Gln Gly
1               5                   10                  15

Gly Ser Thr Ser Ile Ala Cys Pro Asn Gly Cys Gln Ala Ile Ala Asp
            20                  25                  30

Thr Gly Thr Ser Leu Ile Ala Gly Pro Lys Ala Gln Val Glu Ala Ile
        35                  40                  45

Gln Lys Tyr Ile Gly Ala Glu Pro Leu
    50                  55

<210> SEQ ID NO 39
<211> LENGTH: 58
<212> TYPE: PRT
<213> ORGANISM: Artificial Sequence
<220> FEATURE:
<223> OTHER INFORMATION: Synthetic peptide Fragment 5 homolog from
      Ancylostoma duodenale

<400> SEQUENCE: 39

Val Thr Arg Arg Gly Tyr Trp Gln Phe Lys Met Asp Lys Val Gln Gly
1               5                   10                  15

Gly Ser Thr Ser Ile Ala Cys Pro Asn Gly Cys Gln Ala Ile Ala Asp
            20                  25                  30

Thr Gly Thr Ser Leu Ile Ala Gly Pro Lys Ala Gln Val Glu Ala Ile
        35                  40                  45

Gln Lys Tyr Ile Gly Ala Glu Pro Leu Met
    50                  55

<210> SEQ ID NO 40
<211> LENGTH: 59
<212> TYPE: PRT
<213> ORGANISM: Artificial Sequence
<220> FEATURE:
<223> OTHER INFORMATION: Synthetic peptide Fragment 5 homolog from
      Ancylostoma caninum

<400> SEQUENCE: 40

```
Val Thr Arg Arg Gly Tyr Trp Gln Phe Lys Met Asp Lys Val Gln Gly
1               5                   10                  15

Gly Ser Thr Ser Ile Ala Cys Pro Asn Glu Phe Ser Gly Cys Gln Ala
                20                  25                  30

Ile Ala Asp Thr Gly Thr Ser Leu Ile Ala Gly Pro Lys Ala Gln Ser
            35                  40                  45

Arg Ala Ser Arg Asn Ser Leu Val Leu Glu Pro
    50                  55
```

<210> SEQ ID NO 41
<211> LENGTH: 57
<212> TYPE: PRT
<213> ORGANISM: Artificial Sequence
<220> FEATURE:
<223> OTHER INFORMATION: Synthetic peptide Fragment 5 homolog from
      Schistosoma mansoni

<400> SEQUENCE: 41

```
Leu Thr Glu Gln Ser Tyr Trp Leu Phe Lys Met Asp Lys Leu Thr Ile
1               5                   10                  15

Ser Ser Asp Met Thr Ala Cys Pro Asp Gly Cys Leu Ala Ile Ala Asp
                20                  25                  30

Thr Gly Thr Ser Met Ile Ala Gly Pro Thr Asp Glu Ile Gln Lys Ile
            35                  40                  45

Asn Ala Lys Leu Gly Ala Thr Arg Leu
    50                  55
```

<210> SEQ ID NO 42
<211> LENGTH: 57
<212> TYPE: PRT
<213> ORGANISM: Artificial Sequence
<220> FEATURE:
<223> OTHER INFORMATION: Synthetic peptide Fragment 5 homolog from
      Opisthorchis viverrini

<400> SEQUENCE: 42

```
Leu Thr His Glu Ala Tyr Trp Gln Phe Lys Val Asp Ser Met Ser Val
1               5                   10                  15

Gly Gly Met Lys Leu Cys Glu Asn Gly Cys Gln Ala Ile Ala Asp Thr
                20                  25                  30

Gly Thr Ser Leu Ile Ala Gly Pro Ser Glu Glu Val Gly Lys Leu Asn
            35                  40                  45

Asp Ala Leu Gly Ala Ile Lys Leu Pro
    50                  55
```

<210> SEQ ID NO 43
<211> LENGTH: 53
<212> TYPE: PRT
<213> ORGANISM: Artificial Sequence
<220> FEATURE:
<223> OTHER INFORMATION: Synthetic peptide Fragment 5 homolog from
      Fasciola hepatica

<400> SEQUENCE: 43

```
Val Thr His Glu Ala Tyr Trp Gln Phe Lys Val Asp Lys Ile Glu Phe
1               5                   10                  15

Pro Gly Val Ser Ile Cys Ala Asp Gly Cys Gln Ala Ile Ala Asp Thr
                20                  25                  30

Gly Thr Ser Leu Ile Ala Gly Pro Lys Lys Glu Val Cys Ala Leu Asn
            35                  40                  45

Glu Gln Ile Gly Gly
```

-continued

<210> SEQ ID NO 44
<211> LENGTH: 55
<212> TYPE: PRT
<213> ORGANISM: Artificial Sequence
<220> FEATURE:
<223> OTHER INFORMATION: Synthetic peptide Fragment 5 homolog from
      Brugia malayi

<400> SEQUENCE: 44

Val Ser Arg His Gly Tyr Trp Gln Phe Lys Met Asp Arg Val Leu Gly
 1               5                  10                  15

Arg Gly Lys Ala Ile Gly Cys Gly Asn Gly Cys Gln Ala Ile Ala Asp
            20                  25                  30

Thr Gly Thr Ser Leu Ile Ala Gly Pro Lys Ser Gln Ile Asp Lys Ile
        35                  40                  45

Gln Glu Tyr Ile Gly Ala Glu
    50                  55

<210> SEQ ID NO 45
<211> LENGTH: 58
<212> TYPE: PRT
<213> ORGANISM: Artificial Sequence
<220> FEATURE:
<223> OTHER INFORMATION: Synthetic peptide Fragment 5 homolog from
      Onchocerca volvulus

<400> SEQUENCE: 45

Val Ser Arg His Gly Tyr Trp Gln Phe Lys Met Asp Ser Ile Gln Gly
 1               5                  10                  15

Lys Asp Glu Ala Ile Gly Cys Ala Asn Gly Cys Gln Ala Ile Ala Asp
            20                  25                  30

Thr Gly Thr Ser Leu Ile Ala Gly Gln Lys Val Lys Leu Ile Lys Phe
        35                  40                  45

Ser Asn Ile Leu Val Leu Asn Met Cys Met
    50                  55

<210> SEQ ID NO 46
<211> LENGTH: 58
<212> TYPE: PRT
<213> ORGANISM: Artificial Sequence
<220> FEATURE:
<223> OTHER INFORMATION: Synthetic peptide Fragment 5 homolog from
      Human pepsinogen

<400> SEQUENCE: 46

Val Thr Val Glu Gly Tyr Trp Gln Ile Thr Val Asp Ser Ile Thr Met
 1               5                  10                  15

Asn Gly Glu Ala Ile Ala Cys Ala Glu Gly Cys Gln Ala Ile Val Asp
            20                  25                  30

Thr Gly Thr Ser Leu Leu Thr Gly Pro Thr Ser Pro Ile Ala Asn Ile
        35                  40                  45

Gln Ser Asp Ile Gly Ala Ser Glu Asn Ser
    50                  55

<210> SEQ ID NO 47
<211> LENGTH: 59
<212> TYPE: PRT
<213> ORGANISM: Artificial Sequence
<220> FEATURE:
<223> OTHER INFORMATION: Synthetic peptide Fragment 5 homolog from
      Human cathepsin D

```
<400> SEQUENCE: 47

Val Thr Arg Lys Ala Tyr Trp Gln Val His Leu Asp Gln Val Glu Val
1               5                   10                  15

Ala Ser Ser Gly Leu Thr Leu Cys Lys Glu Gly Cys Glu Ala Ile Val
            20                  25                  30

Asp Thr Gly Thr Ser Leu Met Val Gly Pro Val Asp Glu Val Arg Glu
        35                  40                  45

Leu Gln Lys Ala Ile Gly Ala Val Pro Leu Ile
    50                  55

<210> SEQ ID NO 48
<211> LENGTH: 58
<212> TYPE: PRT
<213> ORGANISM: Artificial Sequence
<220> FEATURE:
<223> OTHER INFORMATION: Synthetic peptide Fragment 5 homolog from
      Human renin

<400> SEQUENCE: 48

Leu Ile Lys Thr Gly Val Trp Gln Ile Gln Met Lys Gly Val Ser Val
1               5                   10                  15

Gly Ser Ser Thr Leu Leu Cys Glu Asp Gly Cys Leu Ala Leu Val Asp
            20                  25                  30

Thr Gly Ala Ser Tyr Ile Ser Gly Ser Thr Ser Ser Ile Glu Lys Leu
        35                  40                  45

Met Glu Ala Leu Gly Ala Lys Lys Arg Leu
    50                  55
```

MULTIVALENT ANTIHELMINTHIC VACCINE

RELATED APPLICATION

This application claims benefit of U.S. Provisional Application No. 61/077,256, filed Jul. 1, 2008.

BACKGROUND OF THE INVENTION

1. Field of the Invention

The invention generally relates to a multivalent anthelminthic vaccine that targets both hookworm and schistosomiasis. In particular, the invention provides a vaccine that includes at least two hookworm antigens, of which one is a third-stage larval stage antigen and one is an adult stage antigen, and at least one schistosome antigen. In some cases, full or partial sequences of schistosome antigens may be fused with full or partial sequences of hookworm (*Necator americanus*) to produce recombinant chimeric antigens.

2. Background of the Invention

Hookworm infection and schistosomiasis are the two most important parasitic helminth infections of humans. Together these two helminthiases are responsible for an estimated 345,000 deaths and 26.6 million disability adjusted life years (DALYs) annually making them second only to malaria as the most important causes of human parasitic infection (Table 1).

SUMMARY OF THE INVENTION

It is an object of this invention to provide multivalent anthelminthic vaccines that target both hookworm and schistosomiasis. The multivalent anthelminthic vaccine includes one or more recombinant hookworm antigens and one or more recombinant schistosome antigens. In some embodiments, the vaccine contains 1) at least one recombinant hookworm third-stage larval antigen; 2) at least one recombinant hookworm adult stage antigen; and 3) at least one recombinant schistosome antigen. By "antigen" it should be understood that full length sequences or fragments with antigenic sequences, i.e. capable of causing the body to raise antibody titers for protection against hookworm and schistosome infection, can be used in the practice of the invention. In some embodiments, the one or more recombinant hookworm antigens are *Necator americanus* hookworm antigens such as, for example Na-ASP-2, Na-SAA-2, Na-APR-1 and Na-GST-1. In other embodiments, *Necator americanus* hookworm antigens such as, Na-APR-2, Na-CP-2, Na-CP-3, Na-CP-4 and Na-CP-5 may be employed. In yet other embodiments, full or partial sequences of one or more different *Necator americanus* antigens may be linked to produce recombinant chimeric antigens. An example of this is a chimeric protein comprised of Na-GST-1 linked to a fragment of Na-APR-1 (e.g. fragment 5, described below).

TABLE 1

Disease burden of hookworm and schistosomiasis and comparison with malaria

| Disease | Global Prevalence | Major Geographic Regions | Deaths | DALYs (Disability adjusted life years) | Major clinical features and disabilities |
|---|---|---|---|---|---|
| Hookworm Infection (Major species: *Necator americanus*; Minor species: *Ancylostoma duodenale*) | 576 million | Sub-Saharan Africa, SE Asia, Brazil | 65,000 | 22.1 million | Anemia, physical & cognitive retardation |
| Schistosomiasis (Major species: *Schistosoma mansonia* and *Schistosoma haematobium*; Minor species: *Schistosoma japonicum*) | 207 million | Sub-Saharan Africa, Brazil | 280,000 | 4.5 million | Anemia, liver disease, urogenital disease and physical & cognitive retardation |
| Hookworm and Schistosomiasis | | Sub-Saharan Africa, Brazil | 345,000 | 26.6 million | |
| Malaria | 300-500 million | Sub-Saharan Africa | 1,200,000 | 46.5 million | Anemia, cerebral malaria, Acute Respiratory Distress Syndrome (ARDS) |

Both hookworm and schistosomiasis are co-endemic in many regions of the world. In both sub-Saharan Africa and Brazil these two helminth infections not only exhibit a high degree of geographic overlap, but there is evidence that co-infections with hookworm and schistosomes are extremely common, and there is evidence that hookworm promotes susceptibility to schistosomiasis (Fleming et al, 2006; Raso et al, 2007). The co-morbid effects of hookworm and schistosomiasis are profound and include severe anemia and physical and intellectual growth retardation in children, as well as adverse pregnancy outcome (Hotez and Ferris, 2006; Hotez et al, 2006). There is additional evidence that both hookworm and schistosomiasis increase susceptibility and worsen the severity of malaria and HIV/AIDS (Hotez et al, 2006; 2007).

In other embodiments, the adult stage and third-stage larval hookworm antigens are *Ancylostoma duodenale* hookworm antigens.

In some embodiments of the invention, the one or more recombinant schistosome antigens are *Schistosoma mansoni* antigens, for example, Sm-TSP-2, Sm-TSP-3, Sm-TSP-4 and Sm-29. In other embodiments, the one or more recombinant schistosome antigens are *Schistosoma haematobium* antigens, for example, Sh-TSP-2. In yet other embodiments, the one or more recombinant schistosome antigens are *Schistosoma japonicum* antigens. In other embodiments full or partial sequences of schistosome antigens may be fused with full or partial sequences of hookworm (e.g. *Necator americanus*) to produce recombinant chimeric antigens. Examples of these chimeric proteins include but are not limited to the second extracellular domain (EC-2) of Sm-TSP-2 linked to Na-GST-1, or the EC-2 of Sm-TSP-2 linked to a fragment of Na-APR-1.

In addition, the multivalent anthelminthic vaccine may also include one or more adjuvants. Examples of suitable adjuvants include but are not limited to an aluminum-based adjuvant, CpG and Synthetic Lipid A.

BRIEF DESCRIPTION OF THE DRAWINGS

FIGS. 1A and B. Na-ASP-2: A, nucleic acid sequence; B, amino acid sequence.

FIGS. 2A and B. Na-SAA-2: A, nucleic acid sequence; B, amino acid sequence.

FIG. 3A-D. Na-APR-1: A, nucleic acid sequence encoding Na-APR-1, Shanghai strain; B, amino acid sequence of Na-APR-1, Shanghai strain; C, nucleic acid sequence encoding Na-APR-1, Australian strain; D, amino acid sequence of Na-APR-1, Australian strain.

FIGS. 4A and B. Na-CP-2: A, nucleic acid sequence; B, amino acid sequence.

FIGS. 5A and B. Na-CP-3: A, nucleic acid sequence; B, amino acid sequence.

FIGS. 6A and B. Na-CP-4: A, nucleic acid sequence; B, amino acid sequence.

FIGS. 7A and B. Na-CP-5: A, nucleic acid sequence; B, amino acid sequence.

FIGS. 8A and B. Na-GST-1; A, nucleic acid sequence; B, amino acid sequence.

FIGS. 9A and B. Sm-TSP-2: A, nucleic acid sequence; B, amino acid sequence. Residues corresponding to extracellular loop-2 (EC-2) are underlined.

FIGS. 10A and B. Sm-29: A, nucleic acid sequence; B, amino acid sequence.

FIGS. 11A and B. Sh-TSP-2: A, nucleic acid sequence; B, amino acid sequence.

FIGS. 12A and B. Sm-TSP-3: A, nucleic acid sequence; B, amino acid sequence.

FIGS. 13A and B. Sm-TSP-4: A, nucleic acid sequence; B, amino acid sequence.

FIGS. 14A and B. Na-APR-2: A, nucleic acid sequence; B, amino acid sequence.

FIG. 15A-C. Chimera including Na-GST-1 and fragment 5 of Na-APR-1. A, schematic of the construct; B, nucleic acid sequence C, amino acid sequence. Solid underline=Na-GST-1; dotted underline=fragment 5; no underline (between Na-GST-1 and fragment 5)=linker; no underline (after fragment 5)=histidine tag.

FIG. 16A-C. Chimera including Sm-TSP-2 EC-2 and fragment 5 of Na-APR-1. A, schematic of the construct; B. nucleic acid sequence; C, amino acid sequence. Solid underline=Sm-TSP-2-extracellular loop-2 (EC-2); dotted underline=fragment 5; no underline (between Sm-TSP-2-EC-2 and fragment 5)=linker; no underline (after fragment 5)=histidine tag.

FIG. 17A-C. Chimera including Na-GST-1 and Sm-TSP-2 EC-2. A, schematic of the construct; B. nucleic acid sequence; C, amino acid sequence. Solid underline=Na-GST-1; dotted underline=Sm-TSP-2 EC-2; no underline (between Na-GST-1 and Sm-TSP-2 EC-2)=linker; no underline (after Sm-TSP-2 EC-2)=histidine tag.

FIG. 18. Parasite gut immunolocalization of three Na-APR-1 monoclonal antibodies Each of these monoclonal antibodies exhibits the ability to inhibit Na-APR-1 enzymatic activity (see FIG. 19)

FIG. 21. Amino acid sequence of Na-APR-1 fragment 5 (*Necator americanus*) and its orthologues in other parasitic helminths. *Necator americanus*, SEQ ID NO:37; *Ancylostoma ceylanicum*, SEQ ID NO:38; *Ancylostoma duodenale*, SEQ ID NO:39; *Anclostoma canimun*, SEQ ID NO:40; *Schistosoma mansoni*, SEQ ID NO:41; *Opisthorchis viverrini*, SEQ ID NO:42; *Fasciola hepatica*, SEQ ID NO:43; *Brugia malayi*, SEQ ID NO:44; *Onchocerca volvulus*, SEQ ID NO:45; Human pepsinogen, SEQ ID NO:46; Human cathepsin D, SEQ ID NO:47; Human rennin, SEQ ID NO:48.

DETAILED DESCRIPTION OF THE PREFERRED EMBODIMENTS OF THE INVENTION

Figure 19:
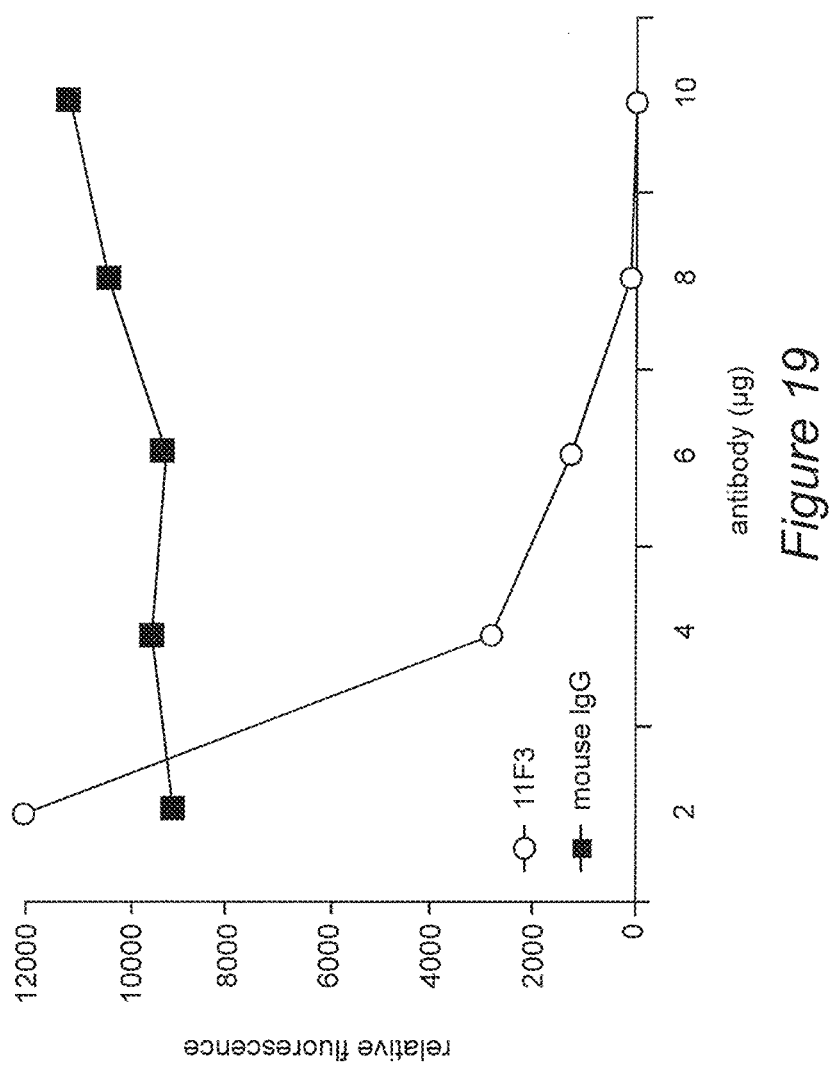
FIG. 19. Monoclonal antibody neutralization of enzymatic activity using mAB 11F3. Similar results with 2H12 and 9E10 antibodies (data not shown).

The present invention is based on the development of a multivalent antithelminthic vaccine (MAHV) that targets both hookworm and schistosomiasis. The high frequency of polyparasitsm with hookworms and schistosomes and the co-morbidity and synergy with malaria and HIV/AIDS provided the impetus for the development of the vaccine. The MAHV of the invention comprises at least two recombinant hookworm antigens and at least one schistosome antigen. In some embodiments, one of the hookworm antigens is a third-stage larval antigen and another of the hookworm antigens is an adult stage antigen. Preferably, the antigens are from species of worms that infect humans, although this may not always be the case. For example, preferred hookworm antigens include *N. americanus* antigens and preferred schistosome antigens include *S. mansoni* antigens (which may be surface or adult stage antigens) and *S. haematobium* antigens (especially surface antigens). Preferably, the antigens are from major species as listed in Table 1, e.g. *Necator americanus* for hookworm and *Schistosoma mansonia* and *Schistosoma haematobium* for schistosomes. However, several orthologous proteins from other minor species may also be used, including but not limited to *Ancylostoma duodenale* for hookworm and *Schistosoma japonicum* for schistosomes.

To reduce the number of antigens in the MAHV, in some cases recombinant chimeric or fusion proteins are created. For example, the Na-GST-1 gene product may be expressed in a Na-GST-1-Sm-TSP-2 EC-2 (EC-2 is described in detail below) hookworm/schistosome recombinant fusion protein or a hookworm/schistosome fusion recombinant protein comprised of Sm-TSP-2 EC-2 and a partial length fragment of Na-APR-1 such as fragment 5 (which is described in detail below). A hookworm chimeric recombinant protein comprised of Na-GST-1 linked to a partial length fragment of Na-APR-1 (e.g. fragment 5) may also be produced.

The development of a MAHV for hookworm and schistosomiasis combined represents a major global public health breakthrough, and will facilitate meeting several goals such as sustainable poverty reduction, eradicating poverty and hunger, achieving universal primary education, reducing child mortality, improving maternal health, and combating HIV/AIDS, malaria, and other diseases.

Table 2 lists several exemplary candidate *N. americanus, S. mansoni* and *S. haematobium* antigens that may be used in the practice of the present invention, each of which exhibits strong preclinical evidence for protective immunity.

TABLE 2

Candidate antigens for the multivalent antithelminthic vaccine

| | Major Reference |
|---|---|
| *Necator americanus* hookworm antigens | |
| Na-ASP-2 | Asojo et al, 2005; Goud et al, 2005 |
| Na-SAA-2 | Fujiwara et al, 2006 |
| Na-GST-1 | Asojo et al, 2007 |
| Na-APR-1 | Loukas et al, 2005; Yang, Y. et al 2009 |
| Na-APR-2 | Williamson et al., 2003 |
| *Schistosoma mansoni* antigens | |
| Sm-TSP-2 and Sm-TSP-2 EC-2 | Tran et al, 2006, Loukas et al unpublished data |
| Sm-TSP-3 | |
| Sm-TSP-4 | |
| Sm-29 | Cardoso et al, 2006 |
| *Schistosoma haematobium* antigens | |
| Sh-TSP-2 (orthologue of Sm-TSP-2) and Sh-TSP-2 EC2 | |
| Sh-TSP-3 (orthologue of Sm-TSP-3) | |
| Sh-TSP-4 (orthologue of Sm-TSP-4) | |
| Sh-29 (orthologue of Sm-29) | |
| Recombinant fusion proteins | |
| Na-GST-1 - Na-APR-1 fragment 5 | |
| Na-GST-1 - Sm-TSP-2 EC2 | |
| Sm-TSP-2 EC2 - Na-APR-1 fragment 5 | |

The amino acid sequences of several suitable antigens and antigenic sequences, as well as the nucleic acid sequences which encode them, are provided in FIGS. 1-17. However, those of skill in the art will recognize that many variants of the sequences presented herein may exist or be constructed which would also function as antigens in the practice of the present invention. For example, with respect to amino acid sequences, variants may exist or be constructed which display: conservative amino acid substitutions; non-conservative amino acid substitutions; truncation by, for example, deletion of amino acids at the amino or carboxy terminus, or internally within the molecule; or by addition of amino acids at the amino or carboxy terminus, or internally within the molecule (e.g. the addition of a histidine tag for purposes of facilitating protein isolation, the substitution of residues to alter solubility properties, the replacement of residues which comprise protease cleavage sites to eliminate cleavage and increase stability, the addition or elimination of glycosylation sites, and the like, or for any other reason). Such variants may be naturally occurring (e.g. as a result of natural variations between species, strains, or individuals, such as Na-APR-1 Shanghai and Australia, FIGS. 3A-D); or they may be purposefully introduced (e.g. in a laboratory setting using genetic engineering techniques). All such variants of the sequences disclosed herein are intended to be encompassed by the teaching of the present invention, provided the variant antigen displays sufficient identity to the described sequences. Preferably, identity will be in the range of about 50 to 100%, or in the range of about 75 to 100%, or in the range of about 80 to 100%, or 85% to 100%, or 90% to 100%, or about 95, 96, 97, 98, 99 or 100% of the disclosed sequences.

The identity is with reference to the portion of the amino acid sequence that corresponds to the original antigen sequence, i.e. not including additional elements that might be added, such as, for example, histidine tags, spacer or linker sequences between antigens in a chimeric construct that encodes multiple antigens, etc. Representative spacer sequences are depicted in FIGS. 15-17. Those of skill in the art will recognize that other suitable spacer sequences might be used in the constructs depicted in these figures, or in some cases, spacer sequences may not be necessary, i.e. they may be eliminated and thus not be present. The same is true for the His tag that is depicted. Other sequences suitable for tracking or purifying and isolating the proteins/polypeptides that contain the antigens may be used to either replace the His tag, or may, in some embodiments, be eliminated, i.e. may not be present.

The MAHV of the invention may be constructed in any of several ways. As stated above, the MAHV may comprise either peptide/protein antigens that are administered directly to a vaccine recipient or nucleic acid (e.g. DNA, stabilized RNA, etc.) that encodes the antigens. The ensuing discussion is intended to apply to both of these possibilities.

The particular design of the vaccine and the arrangement of the antigenic elements of which the vaccine is comprised may vary. For example, the antigens may be administered as a mixture of individual antigens, or as a mixture of chimeric constructs that contain two or more of the antigens (e.g. as depicted in FIGS. 15-17), or even as a single chimeric construct that contains all the antigens of the vaccine. Those of skill in the art will recognize that in a chimeric protein construct, individual antigenic sequences may be separated by linking or spacer sequences which may or may not be antigenic. Thus, in a DNA molecule that encodes a plurality of antigenic sequences, those sequences may be separated spatially by intervening sequences that are translated into linking or spacer sequences, or the intervening sequences may encode genetic elements (e.g. internal ribosomal entry sites, IRES) that result in the translation of separate polypeptides for some or all of the antigens. In addition, other beneficial sequences may also be included. For example: sequences which aid in isolation and purification of the protein (e.g. histidine tag, GST, and maltose binding protein); sequences which direct the protein to a particular intracellular location (e.g. yeast secretory protein); sequences that increase the antigenicity of the protein (e.g. KHL, haptens). Further, various non-coding sequences may be added to nucleic acid vaccine compositions, e.g. to enhance protein expression, promote stability, etc.

Those of skill in the art will recognize that it may not be necessary to utilize the entire primary sequence of a protein or polypeptide in order to elicit an adequate antigenic response to the parasite from which the antigen originates. In some cases, a fragment of the protein is adequate to confer immunization. Thus, the present invention also encompasses antigenic fragments of the sequences disclosed herein, and their use in vaccine preparations. In general, such a fragment will be at least about 10-13 amino acids in length. Those of skill in the art will recognize that suitable sequences are often hydrophilic in nature, and are frequently surface accessible. For example, extracellular Loop 2 of *S. mansoni* Sm-TSP-2 (EC2) or an orthologous loop sequence from another schistosome species and/or genus may be utilized; as may "Fragment 5" from Na-APR-1 as described below, or corresponding, orthologous sequences from other hookworm species and/or genera (e.g. *S. mansoni* cathepsin D). A "corresponding" or "orthologous" sequence is a sequence from a related genus species that exhibits at least about 50, preferably at least about 75%, or more preferably 80, 85, 90, 95, or even 100% nucleic acid homology or encoded amino acid primary sequence identity. Alternatively, even if the level of homology or identity is not at least about 50% or greater, the secondary and/or tertiary structural elements of corresponding or orthologous sequences may be analogous and may perform the same function, and all such sequences are intended to be encompassed by the present invention.

Examples of using peptide fragments or chimeric proteins comprised of full-length peptides and peptide fragments include but are not limited to Na-GST-1 and/or Sm-TSP-2 EC2 fused with a fragment of Na-APR-1, e.g. "fragment 5" of Na-APR-1 (FIGS. 15A-C and 16A-C) or Na-GST-1 combined with Sm-TSP-2 EC2 (FIG. 17A-C). Through testing of monoclonal antibodies against Na-APR-1 a specific fragment known as "fragment 5" was identified as critical for the enzymatic activity of this molecule (see Example 2), and this fragment may be used alone or in combination with other antigens for production and use of vaccines as described herein.

With respect to the nucleic acid sequences disclosed herein, those of skill in the art will recognize that many variants of the sequences may exist or be constructed which would still function to provide the encoded antigens or desired portions thereof. For example, due to the redundancy of the genetic code, more than one codon may be used to code for an amino acid. Further, as described above, changes in the primary sequence of the antigen may be desired, and this would necessitate changes in the encoding nucleic acid sequences. In addition, those of skill in the art will recognize that many variations of the nucleic acid sequences may be constructed for purposes related to cloning strategy, (e.g. for ease of manipulation of a sequence for insertion into a vector, such as the introduction of restriction enzyme cleavage sites, etc.), for purposes of modifying transcription (e.g. the introduction of promoter or enhancer sequences, and the like), or for any other suitable purpose. In addition, *Pichia pastoris* or *Escherichia coli* optimized coding sequences may be utilized. In one embodiment, the sequences used in the vaccine are produced in *Pichia*. All such variants of the nucleic acid sequences disclosed herein are intended to be encompassed by the present invention, provided the sequences display about 50 to 100% identity to the original sequence and preferably about 75 to 100% identity, and more preferably about 80 to 100% identity, and most preferably 95, 96, 97, 98, 99 or 100% identity. The identity is with reference to the portion of the nucleic acid sequence that corresponds to the original sequence, and is not intended to cover additional elements such as promoters, vector-derived sequences, restriction enzyme cleavage sites, etc. derived from other sources.

The vaccine of the invention may also include one or more adjuvants. In a preferred embodiment, the vaccine of the present invention includes an aluminum-based adjuvant such as the aluminum hydroxide adjuvant Alhydrogel® either alone or in combination with additional adjuvants such as 10104 CpGs and synthetic lipid A molecules. CpGs is a synthetic oligodeoxynucleotide adjuvant containing cytosine-guanine dinucleotides in particular base contexts or CpG motifs, (e.g. CpG ODN) and is an immunomodulatory molecule. In addition, various lipid A derivatives, including the synthetic lipid A known as gluopyrranosyl lipid A (GLA) may be used as adjuvants (Persing D H, Trends in Microbiology 2002 10 (10 Suppl) S32-7). Lipid A is the portion of lipopolysaccharide that is known to be the primary component with regard to adjuvanticity and toxicity. Derivatives of lipid A have been produced in an attempt to retain the immunostimulatory activity of Lipid A yet reduce the toxicity. One such derivative, monophosphoryl lipid A (MPL, available from Chiron), has been shown to exhibit strong Th1 adjuvant activity but with a considerably reduced toxicity compared to LPS. MPL has adjuvant activity whether used alone, or in combination with other immunostimulants, such as CpG oligodeoxynucleotides (ODN), or an aluminum hydroxide based adjuvant. Another synthetic lipid A derivative that is very similar to the lipopolysaccharide derivative lipid A monophosphoryl (MPL) by Chiron is available from the Infectious Disease Research Institute, Seattle, Wash. Seppic, Quil A is another suitable adjuvant. A publication by McCluskie and Weeratna (Infectious Disorders, 2001, 1, 263-271) gives examples of several different suitable adjuvant systems. Other possible adjuvants include but are not limited to AS04; AS03, a proprietary formulation manufactured by Glaxo Smith Kline that contains an oil-in-water emulsion; AS02A, a proprietary formulation manufactured by Glaxo Smith Kline that contains the same oil-in-water emulsion as in AS03, plus two immunostimulants "3D-MPL" and "QS-21". AS03 and AS02A are described (under their original designations SBAS3 and SBAS2, respectively) in Stoute et al NEJM 1997 336:86-91. It is noted that, AS02A and AS03 are designed to be used with the aluminum based adjuvant AS04, also available from GlaxoSmithKline.

The present invention provides compositions for use in eliciting immune responses to both hookworm and schistosomes. By "eliciting an immune response" we mean that an antigen or antigenic region or epitope stimulates synthesis of specific antibodies at a titer of about >1 to about $1 \times 10^6$ or greater. Preferably, the titer is from about 10,000 to about $1 \times 10^6$ or more, as measured by enzyme Linked Immunosorbent Assay (ELISA) or greater than 1,000 antibody units as defined previously (Malkin et al., 2005a; 2005b). By "vaccine" we mean an antigen or antigen preparation that elicits an immune response that preferably results in a protective immune response. However, those of skill in the art will recognize that many benefits may accrue even if a total protective response does not occur. Thus, the vaccines of the invention may also serve to decrease symptoms of both hookworm and schistosome infection, and thereby provide much benefit to the vaccine recipient. For example, a decrease in hookworm burden of a least about 30% in an organism in relation to a non-vaccinated (e.g. adjuvant alone) control organism represents such an outcome. This worm burden reduction has been calculated to restore a child's daily iron requirements that would otherwise be lost from a moderate (i.e. infections with between 2,000 and 4,000 hookworm eggs per gram of feces) infection with hookworm. Preferably, however, the level of the decrease in hookworm burden would approach 50%, or more. With respect to schistosome burden, the level of decrease in parasite egg production and/or worm burden would exceed 40%, as per standards set previously by the World Health Organization.

The compositions of the invention include substantially purified and/or isolated recombinant hookworm and schistosome antigens or combinations of antigens as described herein, or nucleic acids encoding such antigens, and a pharmacologically suitable carrier. The preparation of such compositions for use as vaccines is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients and/or detergents which are pharmaceutically acceptable and compatible with the active ingredients. Suitable excipients are, for example, water, saline, dextrose, glycerol, ethanol, zwiterrionic detergents and the like, or combinations thereof. In addition, the composition may contain minor amounts of auxiliary substances such as wetting or emulsifying agents, pH buffering agents, and the like. In addition, the composition may contain other adjuvants. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of antigens in the formulations may vary. However, in general, the amount in the formulations will be from about 1-99%.

The present invention also provides methods of eliciting an immune response to hookworm and methods of vaccinating a mammal against both hookworm and schistosome infection. The methods generally involve identifying a suitable vaccine recipient, and administering to the recipient a composition comprising the antigens and adjuvants described herein in a pharmacologically acceptable carrier. The vaccine preparations of the present invention may be administered by any of the many suitable means which are well known to those of skill in the art, including but not limited to by injection, orally, intranasally, by ingestion of a food product containing the antigens, etc. In preferred embodiments, the mode of administration is subcutaneous or intramuscular. The vaccine recipient is typically a mammal, and is usually but not always a human.

Immunization of vaccine recipients may be carried our in conjunction with chemotherapy. For example, in one embodiment, preventive strategy that combines the MAHV with benzimidazoles and praziquantel chemotherapy is utilized. Chemotherapy may be provided before, together with, or after vaccination. However, in a preferred embodiment, chemotherapy is provided to the vaccine recipient prior to vaccine administration.

The invention may be more fully appreciated in light of the ensuing non-limiting Examples.

EXAMPLES

Example 1

Construction of MAHV

The following is a list of suitable exemplary antigen combinations for use in the vaccines of the invention:
1) Na-ASP-2+Na-GST-1+Sm-TSP-2+Adjuvant;
2) Na-ASP-2+Na-APR-1+Sm-TSP-2+Adjuvant;
3) Na-SAA-2+Na-GST-1+Sm-TSP-2+Adjuvant;
4) Na-SAA-2+Na-APR-1+Sm-TSP-2+Adjuvant;
5) Na-ASP-2+Na-GST-1+Sm-29+Adjuvant;
6) Na-ASP-2+Na-APR-1+Sm-29+Adjuvant;
7) Na-SAA-2+Na-GST-1+Sm-29+Adjuvant;
8) Na-SAA-2+Na-APR-1+Sm-29+Adjuvant;
9) Na-APR-1+Na-GST-1+Sm-TSP-2+Adjuvant;
10) Na-APR-1+Na-GST-1+Sm-29+Adjuvant;
11) Chimera of Na-GST-1–Na-APR-1 fragment 5+Sm-TSP-2+Adjuvant;
12) Chimera of Na-GST-1–Sm-TSP EC2+Adjuvant; and
13) Chimera of Sm-TSP 2 EC2–Na-APR-1 fragment 5+Adjuvant;

Example 2

Identification of Na-APR-1 Fragment that is Critical for Enzyme Activity

Figure 20:
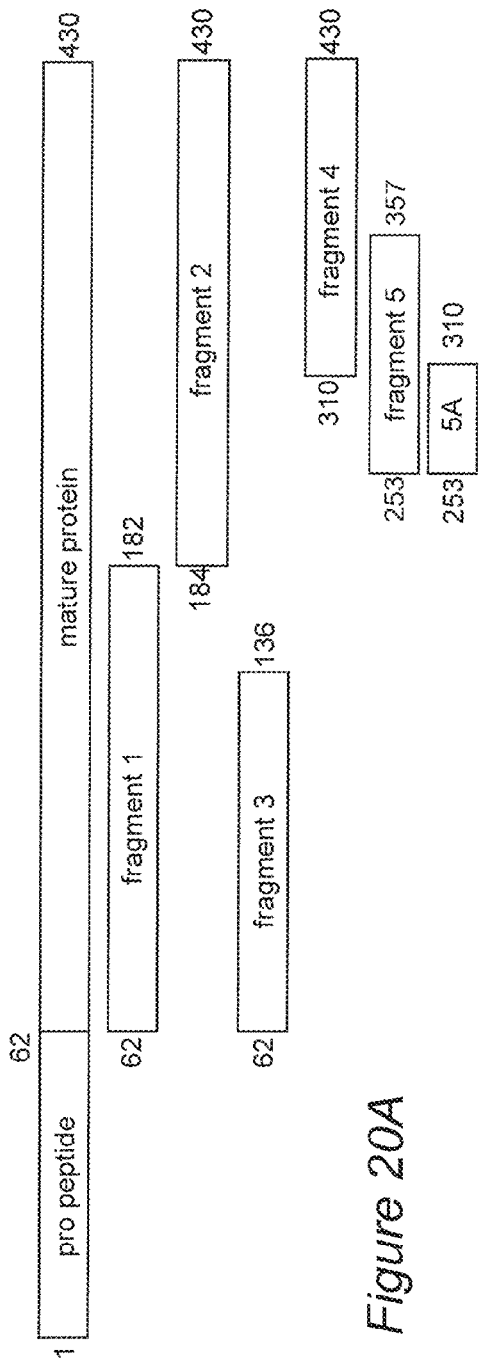
FIGS. 20A and B. Monoclonal antibody mapping to Na-APR-1 fragment 5. A, shows the relative placement of fragments that were tested compared to the mature protein; B, results of binding of antibodies 2H12, 9E10 and 11F3 to Na-APR-1 fragments 1-5.
Figure 21:
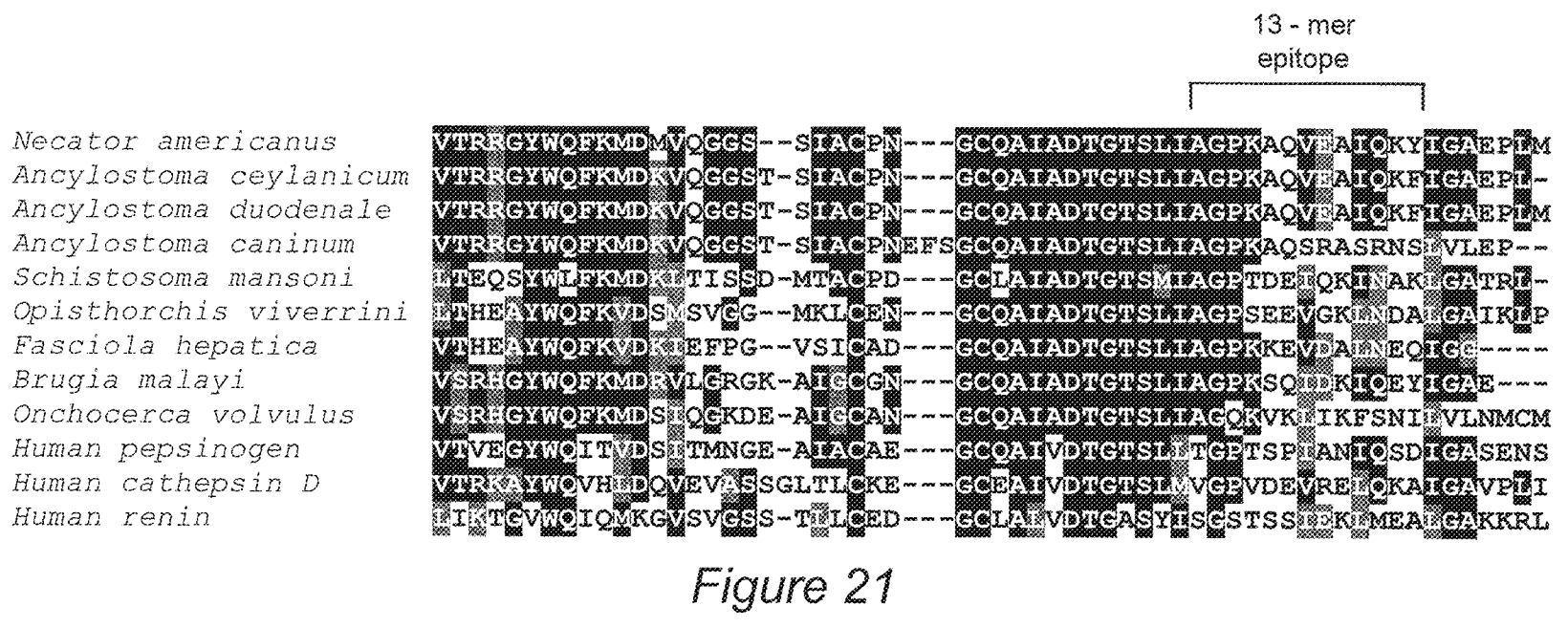
Figure 22:
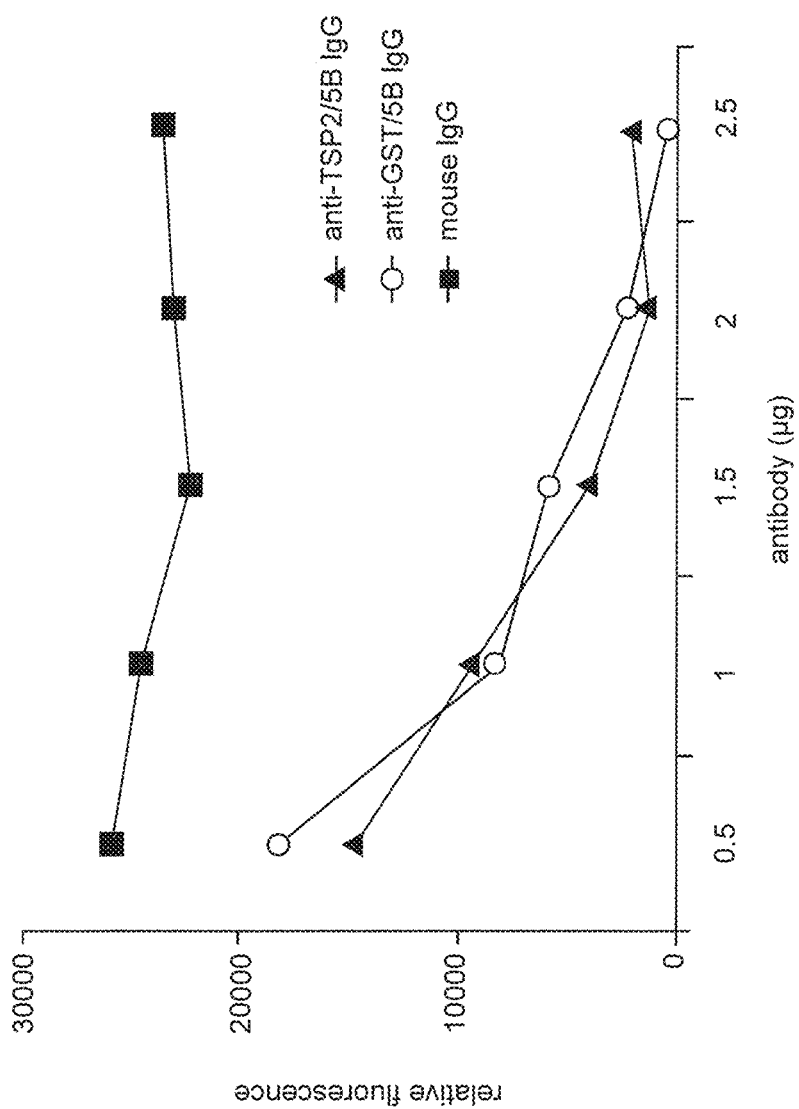
FIG. 22. Antibody against either the Na-GST-1-Na-APR-1 fragment 5 chimeric protein or the Sm-TSP-2 EC2-Na-APR-1 fragment 5 chimeric protein neutralize Na-APR-1 enzymatic activity.

Through testing of monoclonal antibodies against Na-APR-1 a specific fragment known as "fragment 5" was identified as critical for the enzymatic activity of this molecule. The evidence that fragment 5 is a critical Na-APR-1 peptide required for protection against either hookworm or schistosome challenge infections is as follows: As shown in FIG. 18, three monoclonal antibodies against Na-APR-1 known as 2H112, 9E10, and 11F3 bind to the hookworm alimentary canal at the immunolocalized site of Na-APR-1. FIG. 19 shows results obtained when monoclonal antibody (mAB) 11F3 was used to neutralize enzymatic activity of Na-APR-1. As can be seen, a concentration of 10 μg of mAb 11F3 was sufficient to completely eliminate activity. As shown in FIG. 20, these monoclonal antibodies map to a unique fragment of Na-APR-1 known as "fragment 5", the amino acid sequence of which is shown in FIG. 21. Also shown in FIG. 21 are the sequences homologous to Na-APR-1 fragment 5 from several other species. Monoclonal antibodies against fragment 5 of Na-APR-1 immunologically recognize recombinant Na-GST-1–Na-APR-1 fragment 5 chimeric protein, and recombinant Sm-TSP-2 EC2-Na-APR-1 fragment 5 chimeric protein expressed in bacteria (*Escherichia coli*) (data not shown). Conversely, antibodies to these two fusion proteins neutralize the enzymatic activity of Na-APR-1 recombinant enzyme (FIG. 22).

Example 3

Vaccine Comprising the Sm-TSP-2 EC2-Na-APR-1 Fragment 5 Chimeric Protein Causes a Reduction of Worm Burden In Vivo A vaccine composition comprising a chimeric recombinant protein that included schistosome antigen Sm-TSP-2 EC2 fused to hookworm antigen Na-APR-1 fragment 5 ("Sm-TSP-2 EC2-Na-APR-1 fragment 5"; see FIGS. 16A-C for sequence) was prepared and tested in vivo. Briefly, mice were inoculated with Schistosomes according to methods known in the art. A preparation which included the chimeric polypeptide and the adjuvants alum and CpG was administered to experimental mice (n=10). Control mice were inoculated with *Escherichia coli* maltose binding protein plus adjuvant.

After a suitable time period, the worm burdens of the animals were determined. The results showed that mice which received the Sm-TSP-2 EC2-Na-APR-1 fragment 5 chimeric protein showed a 59% reduction in Schistosome worm burden compared to control mice.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

Asojo O A, Goud G, Dhar K, Loukas A, Zhan B, Deumic V, Liu S, Borgstahl G, Hotez P. Novel X-ray structure of Na-ASP-2, a PR-1 protein from the nematode parasite *Necator americanus* and a vaccine antigen for human hookworm infection. J Molec Biol 2005; 346: 801-14.

Asojo O A, Homma K, Sedlacek M, Ngamelue M, Goud G N, Zhan B, Deumic V, Asojo O, Hotez P J. X-ray structures of NaGST-1 and NaGST-2 two glutathione S-transferase from the human hookworm *Necator americanus*. BMC STRUCTURAL BIOLOGY 2007; 7:42.

Cardoso F C, Pinho J M, Azevedo V, Oliveira S C. Identification of a new *Schistosoma mansoni* membrane-bound protein through bioinformatic analysis. Genetic Mol Res 2006; 5: 609-18.

Fleming F M, Brooker S, Geiger S M, Caldas I R, Correa-Oliveira R, Hotez P J, Bethony J M. Synergistic associations between hookworm and other helminth species in a rural community in Brazil. Trop Med Int Health 2006; 11: 56-64.

Goud G N, Bottazzi M E, Zhan B, Mendez S, Deumic V, Pleiskatt J, Liu S, Wang Y, Bueno L, Fujiwara R, Samuel A, Ahn S Y, Solanki M, Asojo O, Wen J, Bethony J M, Loukas A, Roy M, Hotez P J. Expression of *Necator americanus* hookworm larval antigen Na-ASP-2 in *Pichia pastoris* and purification of the recombinant protein for use in human clinical trials. Vaccine 2005; 23: 4754-64.

Hotez P J, Ferris M. The antipoverty vaccines. Vaccine 2006; 24: 5787-99.

Hotez P J, Bethony J, Bottazzi M E, Brooker S, Diemert D, Loukas A. New technologies for the control of human hookworm infection. Trends Parastiol 2006; 22: 327-31.

Hotez P J, Bethony J, Costa Oliveira S, Brindley P J, Loukas A. A multivalent anthelminthic vaccine to prevent hookworm and schistosomiasis. EXPERT REVIEW OF VACCINES 2008; 7: 745-52.

Hotez P J, Brooker S, Bethony J M, Bottazzi M E, Loukas A, Xiao S H. Hookworm infection. N Engl J Med 2004; 351: 799-807.

Hotez P J, Fenwick A, Savioli L, Molyneux D H. Rescuing the "bottom billion" through neglected tropical disease control. LANCET 2009; 373: 1570-4.

Hotez P J, Molyneux D H, Fenwick A, Kumaresan J, Ehrlich Sachs S, Sachs J D, Savioli L. Control of neglected tropical diseases. N Engl J Med 2007; 357: 1018-27.

Hotez P J, Molyneux D H, Fenwick A, Ottesen E, Ehrlich Sachs S, Sachs J D. Incorporating a rapid-impact package for neglected tropical diseases with programs for HIV/AIDS, tuberculosis, malaria. PLoS Med 2006; 3: e102.

Loukas A, Bethony J, Brooker S, Hotez P. Hookworm vaccines—past, present and future. Lancet Infectious Diseases 2006; 6: 733-41.

Loukas A, Bethony J M, Mendez S, Fujiwara R T, Goud G N, Ranjit N, Zhan B, Jones B, Bottazzi M E, Hotez P J. Vaccination with recombinant aspartic hemoglobinase reduces parasite load and blood loss after hookworm infection. PLoS Med 2005; 2: e95.

Pearson M S, Bethony J M, Pickering D A, de Oliveira L M, Jariwala A, Santiago H, Miles A P, Zhan B, Jiang D, Ranjit N, Mulvenna J, Tribolet L, Plieskatt J, Smith T, Bottazzi M E, Jones K, Keegan B, Hotez P J, Loukas A. An enzymatically inactivated hemoglobinase from *Necator americanus* induces neutralizing antibodies against multiple hookworm species and protects dogs against heterologous hookworm infection. FASEB J 2009; [EPub ahead of print].

Ranjit N, Zhan B, Stenzel D J, Mulvenna J, Fujiwara R, Hotez P J, Loukas A. A family of cathepsin B cysteine proteases expressed in the gut of the human hookworm, *Necator americanus*. MOLECULAR AND BIOCHEMICAL PARASITOLOGY 2008; 160: 90-9.

Ranjit N, Zhan B, Hamilton B, Stenzel D, Lowther J, Pearson M, Gorman J, Hotez P, Loukas A. Proteolytic degradation of hemoglobin in the intestine of the human hookworm *Necator americanus*. JOURNAL OF INFECTIOUS DISEASES 2009; 199: 904-12.

Raso G, Vounatsou P, Singer B H, N'Goran E K, Tanner M, Utzinger J. An integrated approach for risk profiling and spatial prediction of *Schistosoma mansoni*-hookworm coinfection. Proc Natl Acad Sci USA 2006; 103: 6934-9.

Tran M H, Pearson M S, Bethony J M, Smyth D J, Jones M K, Duke M, Don T A, McManus D P, Correa-Oliveira R, Loukas A. Tetraspanins on the surface of *Schistosoma mansoni* are protective antigens against schistosomiasis. Nature Med 2006; 12: 835-40.

Williamson, A L, Brindley P J, Abbenante G, Datu B J D, Prociv P, Berry C, Girdwood K, Pritchard D A, Fairlie D P, Hotez P J, Zhan B, Loukas A. Hookworm aspartic protease, Na-APR-2, cleaves human hemoglobin and serum proteins in a host-specific fashion. JID 2003; 187: 484-494.

Xiao S, Zhan B, Xue J, Goud G N, Loukas A, Liu Y, Williamson A, Liu S, Deumic V, Hotez P. The evaluation of recombinant hookworm antigens as vaccines in hamsters (*Mesocricetus auratus*) challenged with human hookworm, *Necator americanus*. EXPERIMENTAL PARASITOLOGY 2008; 118: 32-40.

Yang, Y., Wei, H., Qin, W., Zheng, J. Expression and characterization of aspartic protease gene in eggs and larvae stage of *Ancylostoma caninum* Parasitology Research 2009; 104 (6), pp. 1327-1333.

We claim:

1. A fusion protein including at least one amino acid sequence selected from the group consisting of SEQ ID NO:32, SEQ ID NO:34, and SEQ ID NO:36.

2. The fusion protein as recited in claim 1, having the protein sequences of SEQ ID NO: 32.

3. The fusion protein as recited in claim 1, having the protein sequences of SEQ ID NO: 34.

4. The fusion protein as recited in claim 1, having the protein sequences of SEQ ID NO: 36.

* * * * *